(12) United States Patent
Kim et al.

(10) Patent No.: US 7,041,635 B2
(45) Date of Patent: May 9, 2006

(54) FACTOR VIII POLYPEPTIDE

(75) Inventors: Hun-Taek Kim, Seoul (KR); In-Young Song, Gyeonggi-do (KR); Jae Won Choi, Gyeonggi-Do (KR); Jin-Wook Jang, Gyeonggi-Do (KR); Yong-Kook Kim, Seoul (KR); Ho Soon Lee, Seoul (KE); Yung-Jue Bang, Seoul (KR); Dae-Kee Kim, Seoul (KE)

(73) Assignee: IN2GEN Co., Ltd., Seoul (KR)

( * ) Notice: Subject to any disclaimer, the term of this patent is extended or adjusted under 35 U.S.C. 154(b) by 347 days.

(21) Appl. No.: 10/353,753

(22) Filed: Jan. 28, 2003

(65) Prior Publication Data

US 2004/0147436 A1  Jul. 29, 2004

(51) Int. Cl.
A61K 35/14 (2006.01)
A61K 35/16 (2006.01)
A61K 38/00 (2006.01)

(52) U.S. Cl. .......................... 514/2; 514/802; 514/834; 530/350; 530/380; 530/383; 930/10; 930/100

(58) Field of Classification Search ................ 530/350, 530/380, 383; 930/10, 100; 514/2, 802, 514/834
See application file for complete search history.

(56) References Cited

U.S. PATENT DOCUMENTS 5,399,670 A * 3/1995 Bhattacharya et al. ...... 530/383
2002/0132306 A1 9/2002 Kaufman et al.

FOREIGN PATENT DOCUMENTS

WO   WO 00/24759   5/2000
WO   WO 02/102850 A2   12/2002

OTHER PUBLICATIONS

Langner et al., "Synthesis of biologically active deletion mutants of human factor VIII:C", Behring Inst Mitt. 1988 Apr;(82):16-25.
Nesheim et al., "The Effect of Plasma von Willebrand Factor on the Binding of Human Factor VIII to Thrombin-activated Human Platelets", The Journal of Bioiogical Chemistry 1991, 266(27):17815-17820.
Sandberg et al., "Structural and functional characterization of B-domain deleted recombinant factor VIII", Semin Hematol. 2001 Apr;38(2 Suppl 4):4-12.
Krishnan et al., "Thrombin cleavage analysis of a novel antihaemophilic factor variant, factor VIII delta II", Eur J Biochem. 1991 Feb 14;195(3):637-44.
Lind et al., "Novel forms of B-domain-deleted recombinant factor VIII molecules. Construction and biochemical characterization", Eur J Biochem. Aug. 15, 1995;232(1):19-27.
Bihoreau et al., "Structural and functional characterization of Factor VIII-delta II, a new recombinant Factor VIII lacking most of the B-domain", Biochem J. Jul. 1, 1991;277 ( Pt 1):23-31.
Haack et al., "Analysis of expression kinetics and activity of a new B-domain truncated and full-length FVIII protein in three different cell lines", Ann Hematol 1999, 78:111-116.
Herlitschka et al., "High expression of a B-domain deleted factor VIII gene in a human hepatic cell line", Journal of Biotechnology 1998, 61:165-173.
Sandberg et al., "Structural and functional characteristics of the B-domain-deleted recombinant factor VIII protein, r-VIII SQ", Thromb Haemost. Jan. 2001; 85(1):93-100.
Pipe and Kaufman, "Characterization of a genetically engineered inactivation resistant coagulation factor VIIIa", Proc. Natl. Acad. Sci. USA Oct. 1997, 94:11851-11856.
Brinkhous, K.M. et al., 1985, *Proc. Natl. Acad. Sci. USA*, 82:8752-8756.
Burke, R.L. et al., 1986, *J. Biol. Chem.*, 261(27):12574-12578.
Burton, M. et al., 1999, *Proc. Natl. Acad. Sci. USA*, 96(22):12725-12730.
Chiang, G.G. et al., 1999, *Human Gene Therapy*, 10:61-76.
Donath, M.J. et al., 1995, *Biochem. J.*, 312:49-55.
Eaton, D. et al., 1986, *Biochemistry*, 25:505-512.
Eaton, D. et al., 1986, *Biochemistry*, 25:8343-8347.
Esmon, P.C., et al., 1990, *Blood*, 76(8):1593-1600.
Fay, P.J. et al., 1986, *Biochem. Biophys. Acta*, 871:268-278.
Fay, P.J. et al., 1991, *J. Biol. Chem.*, 266(14):8957-8962.
Girma, J.P. et al., 1987, *Blood*, 70(3):605-611.
Koedam, J.A. et al., 1990, *Eur. J. Biochem.*, 189:229-234.
Koller, B.H. and Smithies, O., 1989, *Proc. Natl. Acad. Sci. USA*, 86:8932-8935.
Michnick, D.A. et al., 1994, *J. Biol. Chem.*, 269(31):20095-20102.
Pavirani, A. et al., 1987, *Biochem Biophys Res Commun.*, 145(1):234-240.
Pittman, D.D. & Kaufman, R. J. 1988, *Proc. Natl. Acad. Sci. USA*, 85:2429-2433.
Pittman, D.D. et al., 1993, *Blood*, 81(11):2925-2935.
Toole, J.J. et al., 1984, *Nature*, 312:342-347.
Toole, J.J. et al., 1986, *Proc. Natl. Acad. Sci. USA*, 83:5939-5942.

(Continued)

*Primary Examiner*—Kathleen M. Kerr
*Assistant Examiner*—Holly Schnizer
(74) *Attorney, Agent, or Firm*—JHK Law; Joseph H. Kim

(57) ABSTRACT

The application discloses Factor VIII polypeptides comprising internal deletions of amino acids within the area of residues 741 to 1689, wherein the thrombin cleavage sites at about 741 and about 1689 are present, and a site at about 1648 is not present, as compared to human Factor VIII.

11 Claims, 10 Drawing Sheets

OTHER PUBLICATIONS

Vehar, G.A. et al., 1984, *Nature*, 312:337-342.
Veltkamp, J.J. et al., 1968, *Thromb. Diath. Haemorrh.*, 19(1):279-303.
Wu, G.Y. and Wu, C.H., 1987, *J. Bio. Chem.*, 262(10):4429-4432.
Zijlstra et al., 1989, *Nature*, 342:435-438.

* cited by examiner

FIGURE 1A

```
1                                                                       70
ATRRYYLGAVELSWDYMQSDLGELPVDARFPPRVPKSFPFNTSVVYKKTLFVEFTVHLFNIAKPRPPWMG
                                                                       140
LLGPTIQAEVYDTVVITLKNMASHPVSLHAVGVSYWKASEGAEYDDQTSQREKEDDKVFPGGSHTYVWQV
                                                                       210
LKENGPMASDPLCLTYSYLSHVDLVKDLNSGLIGALLVCREGSLAKEKTQTLHKFILLFAVFDEGKSWHS
                                                                       280
ETKNSLMQDRDAASARAWPKMHTVNGYVNRSLPGLIGCHRKSVYWHVIGMGTTPEVHSIFLEGHTFLVRN
                                                                       350
HRQASLEISPITFLTAQTLLMDLGQFLLFCHISSHQHDGMEAYVKVDSCPEEPQLRMKNNEEAEDYDDDL
                                                                       420
TDSEMDVVRFDDDNSPSFIQIRSVAKKHPKTWVHYIAAEEEDWDYAPLVLAPDDRSYKSQYLNNGPQRIG
                                                                       490
RKYKKVRFMAYTDETFKTREAIQHESGILGPLLYGEVGDTLLIIFKNQASRPYNIYPHGITDVRPLYSRR
                                                                       560
LPKGVKHLKDFPILPGEIFKYKWTVTVEDGPTKSDPRCLTRYYSSFVNMERDLASGLIGPLLICYKESVD
                                                                       630
QRGNQIMSDKRNVILFSVFDENRSWYLTENIQRFLPNPAGVQLEDPEFQASNIMHSINGYVFDSLQLSVC
                                                                       700
LHEVAYWYILSIGAQTDFLSVFFSGYTFKHKMVYEDTLTLFPFSGETVFMSMENPGLWILGCHNSDFRNR
                                                                       770
GMTALLKVSSCDKNTGDYYEDSYEDISAYLLSKNNAIEPRSFSQNSRHPSTRQKQFNATTIPENDIEKTD
                                                                       840
PWFAHRTPMPKIQNVSSSDLLMLLRQSPTPHGLSLSDLQEAKYETFSDDPSPGAIDSNNSLSEMTHFRPQ
                                                                       910
LHHSGDMVFTPESGLQLRLNEKLGTTAATELKKLDFKVSSTSNNLISTIPSDNLAAGTDNTSSLGPPSMP
                                                                       980
VHYDSQLDTTLFGKKSSPLTESGGPLSLSEENNDSKLLESGLMNSQESSWGKNVSSTESGRLFKGKRAHG
                                                                       1050
PALLTKDNALFKVSISLLKTNKTSNNSATNRKTHIDGPSLLIENSPSVWQNILESDTEFKKVTPLIHDRM
                                                                       1120
LMDKNATALRLNHMSNKTTSSKNMEMVQQKKEGPIPPDAQNPDMSFFKMLFLPESARWIQRTHGKNSLNS
                                                                       1190
GQGPSPKQLVSLGPEKSVEGQNFLSEKNKVVVGKGEFTKDVGLKEMVFPSSRNLFLTNLDNLHENNTHNQ
```

FIGURE 1B

EKKIQEEIEKKETLIQENVVLPQIHTVTGTKNFMKNLFLLSTRQNVEGSYEGAYAPVLQDFRSLNDSTNR 1260

TKKHTAHFSKKGEEENLEGLGNQTKQIVEKYACTTRISPNTSQQNFVTQRSKRALKQFRLPLEETELEKR 1330

IIVDDTSTQWSKNMKHLTPSTLTQIDYNEKEKGAITQSPLSDCLTRSHSIPQANRSPLPIAKVSSFPSIR 1400

PIYLTRVLFQDNSSHLPAASYRKKDSGVQESSHFLQGAKKNNLSLAILTLEMTGDQREVGSLGTSATNSV 1470

TYKKVENTVLPKPDLPKTSGKVELLPKVH1YQKDLFPTETSNGSPGHLDLVEGSLLQGTEGAIKWNEANR 1540

PGKVPFLRVATESSAKTPSKLLDPLAWDNHYGTQIPKEEWKSQEKSPEKTAFKKKDTILSLNACESNHAI 1610

AAINEGQNKPEIEVTWAKQGRTERLCSQNPPVLKRHQREITRTTLQSDQEEIDYDDTISVEMKKEDFDIY 1680

DEDENQSPRSFQKKTRHYFIAAVERLWDYGMSSSPHVLRNRAQSGSVPQFKKVVFQEFTDGSFTQPLYRG 1750

ELNEHLGLLGPYIRAEVEDNIMVTFRNQASRPYSFYSSLISYEEDQRQGAEPRKNFVKPNETKTYFWKVQ 1820

HHMAPTKDEFDCKAWAYFSDVDLEKDVHSGLIGPLLVCHTNTLNPAHGRQVTVQEFALFFTIFDETKSWY 1890

FTENMERNCRAPCNIQMEDPTFKENYRFHAINGYIMDTLPGLVMAQDQRIRWYLLSMGSNENIHSIHFSG 1960

HVFTVRKKEEYKMALYNLYPGVFETVEMLPSKAGIWRVECLIGEHLHAGMSTLFLVYSNKCQTPLGMASG 2030

HIRDFQITASGQYGQWAPKLARLHYSGSINAWSTKEPFSWIKVDLLAPMIIHGIKTQGARQKFSSLYISQ 2100

FIIMYSLDGKKWQTYRGNSTGTLMVFFGNVDSSGIKHNIFNPPIIARYIRLHPTHYSIRSTLRMELMGCD 2170

LNSCSMPLGMESKAISDAQITASSYFTNMFATWSPSKARLHLQGRSNAWRPQVNNPKEWLQVDFQKTMKV 2240

TGVTTQGVKSLLTSMYVKEFLISSSQDGHQWTLFFQNGKVKVFQGNQDSFTPVVNSLDPPLLTRYLRIHP 2310

QSWVHQIALRMEVLGCEAQDLY 2332

A

B

SEQUENCE LISTING

<160> NUMBER OF SEQ ID NOS: 25

<210> SEQ ID NO 1
<211> LENGTH: 2332
<212> TYPE: PRT
<213> ORGANISM: Homo sapiens

<400> SEQUENCE: 1

```
Ala Thr Arg Arg Tyr Tyr Leu Gly Ala Val Glu Leu Ser Trp Asp Tyr
 1               5                  10                  15

Met Gln Ser Asp Leu Gly Glu Leu Pro Val Asp Ala Arg Phe Pro Pro
             20                  25                  30

Arg Val Pro Lys Ser Phe Pro Phe Asn Thr Ser Val Val Tyr Lys Lys
         35                  40                  45

Thr Leu Phe Val Glu Phe Thr Val His Leu Phe Asn Ile Ala Lys Pro
     50                  55                  60

Arg Pro Pro Trp Met Gly Leu Leu Gly Pro Thr Ile Gln Ala Glu Val
 65                  70                  75                  80

Tyr Asp Thr Val Val Ile Thr Leu Lys Asn Met Ala Ser His Pro Val
                 85                  90                  95

Ser Leu His Ala Val Gly Val Ser Tyr Trp Lys Ala Ser Glu Gly Ala
            100                 105                 110

Glu Tyr Asp Asp Gln Thr Ser Gln Arg Glu Lys Glu Asp Asp Lys Val
        115                 120                 125

Phe Pro Gly Gly Ser His Thr Tyr Val Trp Gln Val Leu Lys Glu Asn
    130                 135                 140

Gly Pro Met Ala Ser Asp Pro Leu Cys Leu Thr Tyr Ser Tyr Leu Ser
145                 150                 155                 160

His Val Asp Leu Val Lys Asp Leu Asn Ser Gly Leu Ile Gly Ala Leu
                165                 170                 175

Leu Val Cys Arg Glu Gly Ser Leu Ala Lys Glu Lys Thr Gln Thr Leu
            180                 185                 190

His Lys Phe Ile Leu Leu Phe Ala Val Phe Asp Glu Gly Lys Ser Trp
        195                 200                 205

His Ser Glu Thr Lys Asn Ser Leu Met Gln Asp Arg Asp Ala Ala Ser
    210                 215                 220

Ala Arg Ala Trp Pro Lys Met His Thr Val Asn Gly Tyr Val Asn Arg
225                 230                 235                 240

Ser Leu Pro Gly Leu Ile Gly Cys His Arg Lys Ser Val Tyr Trp His
                245                 250                 255

Val Ile Gly Met Gly Thr Thr Pro Glu Val His Ser Ile Phe Leu Glu
            260                 265                 270

Gly His Thr Phe Leu Val Arg Asn His Arg Gln Ala Ser Leu Glu Ile
        275                 280                 285

Ser Pro Ile Thr Phe Leu Thr Ala Gln Thr Leu Leu Met Asp Leu Gly
    290                 295                 300

Gln Phe Leu Leu Phe Cys His Ile Ser Ser His Gln His Asp Gly Met
305                 310                 315                 320

Glu Ala Tyr Val Lys Val Asp Ser Cys Pro Glu Glu Pro Gln Leu Arg
                325                 330                 335

Met Lys Asn Asn Glu Glu Ala Glu Asp Tyr Asp Asp Asp Leu Thr Asp
            340                 345                 350

Ser Glu Met Asp Val Val Arg Phe Asp Asp Asp Asn Ser Pro Ser Phe
```

```
            355                 360                 365
Ile Gln Ile Arg Ser Val Ala Lys Lys His Pro Lys Thr Trp Val His
        370                 375                 380

Tyr Ile Ala Ala Glu Glu Asp Trp Asp Tyr Ala Pro Leu Val Leu
385                 390                 395                 400

Ala Pro Asp Asp Arg Ser Tyr Lys Ser Gln Tyr Leu Asn Asn Gly Pro
                405                 410                 415

Gln Arg Ile Gly Arg Lys Tyr Lys Lys Val Arg Phe Met Ala Tyr Thr
                420                 425                 430

Asp Glu Thr Phe Lys Thr Arg Glu Ala Ile Gln His Glu Ser Gly Ile
        435                 440                 445

Leu Gly Pro Leu Leu Tyr Gly Glu Val Gly Asp Thr Leu Leu Ile Ile
    450                 455                 460

Phe Lys Asn Gln Ala Ser Arg Pro Tyr Asn Ile Tyr Pro His Gly Ile
465                 470                 475                 480

Thr Asp Val Arg Pro Leu Tyr Ser Arg Arg Leu Pro Lys Gly Val Lys
                485                 490                 495

His Leu Lys Asp Phe Pro Ile Leu Pro Gly Glu Ile Phe Lys Tyr Lys
        500                 505                 510

Trp Thr Val Thr Val Glu Asp Gly Pro Thr Lys Ser Asp Pro Arg Cys
    515                 520                 525

Leu Thr Arg Tyr Tyr Ser Ser Phe Val Asn Met Glu Arg Asp Leu Ala
    530                 535                 540

Ser Gly Leu Ile Gly Pro Leu Leu Ile Cys Tyr Lys Glu Ser Val Asp
545                 550                 555                 560

Gln Arg Gly Asn Gln Ile Met Ser Asp Lys Arg Asn Val Ile Leu Phe
                565                 570                 575

Ser Val Phe Asp Glu Asn Arg Ser Trp Tyr Leu Thr Glu Asn Ile Gln
                580                 585                 590

Arg Phe Leu Pro Asn Pro Ala Gly Val Gln Leu Glu Asp Pro Glu Phe
        595                 600                 605

Gln Ala Ser Asn Ile Met His Ser Ile Asn Gly Tyr Val Phe Asp Ser
    610                 615                 620

Leu Gln Leu Ser Val Cys Leu His Glu Val Ala Tyr Trp Tyr Ile Leu
625                 630                 635                 640

Ser Ile Gly Ala Gln Thr Asp Phe Leu Ser Val Phe Phe Ser Gly Tyr
                645                 650                 655

Thr Phe Lys His Lys Met Val Tyr Glu Asp Thr Leu Thr Leu Phe Pro
        660                 665                 670

Phe Ser Gly Glu Thr Val Phe Met Ser Met Glu Asn Pro Gly Leu Trp
    675                 680                 685

Ile Leu Gly Cys His Asn Ser Asp Phe Arg Asn Arg Gly Met Thr Ala
    690                 695                 700

Leu Leu Lys Val Ser Ser Cys Asp Lys Asn Thr Gly Asp Tyr Tyr Glu
705                 710                 715                 720

Asp Ser Tyr Glu Asp Ile Ser Ala Tyr Leu Leu Ser Lys Asn Asn Ala
                725                 730                 735

Ile Glu Pro Arg Ser Phe Ser Gln Asn Ser Arg His Pro Ser Thr Arg
        740                 745                 750

Gln Lys Gln Phe Asn Ala Thr Thr Ile Pro Glu Asn Asp Ile Glu Lys
    755                 760                 765

Thr Asp Pro Trp Phe Ala His Arg Thr Pro Met Pro Lys Ile Gln Asn
770                 775                 780
```

```
Val Ser Ser Ser Asp Leu Leu Met Leu Leu Arg Gln Ser Pro Thr Pro
785                 790                 795                 800

His Gly Leu Ser Leu Ser Asp Leu Gln Glu Ala Lys Tyr Glu Thr Phe
            805                 810                 815

Ser Asp Asp Pro Ser Pro Gly Ala Ile Asp Ser Asn Asn Ser Leu Ser
        820                 825                 830

Glu Met Thr His Phe Arg Pro Gln Leu His His Ser Gly Asp Met Val
            835                 840                 845

Phe Thr Pro Glu Ser Gly Leu Gln Leu Arg Leu Asn Glu Lys Leu Gly
    850                 855                 860

Thr Thr Ala Ala Thr Glu Leu Lys Lys Leu Asp Phe Lys Val Ser Ser
865                 870                 875                 880

Thr Ser Asn Asn Leu Ile Ser Thr Ile Pro Ser Asp Asn Leu Ala Ala
                885                 890                 895

Gly Thr Asp Asn Thr Ser Ser Leu Gly Pro Pro Ser Met Pro Val His
            900                 905                 910

Tyr Asp Ser Gln Leu Asp Thr Thr Leu Phe Gly Lys Lys Ser Ser Pro
        915                 920                 925

Leu Thr Glu Ser Gly Gly Pro Leu Ser Leu Ser Glu Glu Asn Asn Asp
930                 935                 940

Ser Lys Leu Leu Glu Ser Gly Leu Met Asn Ser Gln Glu Ser Ser Trp
945                 950                 955                 960

Gly Lys Asn Val Ser Ser Thr Glu Ser Gly Arg Leu Phe Lys Gly Lys
            965                 970                 975

Arg Ala His Gly Pro Ala Leu Leu Thr Lys Asp Asn Ala Leu Phe Lys
        980                 985                 990

Val Ser Ile Ser Leu Leu Lys Thr Asn Lys Thr Ser Asn Asn Ser Ala
        995                 1000                1005

Thr Asn Arg Lys Thr His Ile Asp Gly Pro Ser Leu Leu Ile Glu
    1010                1015                1020

Asn Ser Pro Ser Val Trp Gln Asn Ile Leu Glu Ser Asp Thr Glu
    1025                1030                1035

Phe Lys Lys Val Thr Pro Leu Ile His Asp Arg Met Leu Met Asp
    1040                1045                1050

Lys Asn Ala Thr Ala Leu Arg Leu Asn His Met Ser Asn Lys Thr
    1055                1060                1065

Thr Ser Ser Lys Asn Met Glu Met Val Gln Gln Lys Lys Glu Gly
    1070                1075                1080

Pro Ile Pro Pro Asp Ala Gln Asn Pro Asp Met Ser Phe Phe Lys
    1085                1090                1095

Met Leu Phe Leu Pro Glu Ser Ala Arg Trp Ile Gln Arg Thr His
    1100                1105                1110

Gly Lys Asn Ser Leu Asn Ser Gly Gln Gly Pro Ser Pro Lys Gln
    1115                1120                1125

Leu Val Ser Leu Gly Pro Glu Lys Ser Val Glu Gly Gln Asn Phe
    1130                1135                1140

Leu Ser Glu Lys Asn Lys Val Val Val Gly Lys Gly Glu Phe Thr
    1145                1150                1155

Lys Asp Val Gly Leu Lys Glu Met Val Phe Pro Ser Ser Arg Asn
    1160                1165                1170

Leu Phe Leu Thr Asn Leu Asp Asn Leu His Glu Asn Asn Thr His
    1175                1180                1185
```

-continued

| | | | | | | | | | | | |
|---|---|---|---|---|---|---|---|---|---|---|---|
| Asn | Gln | Glu | Lys | Lys | Ile | Gln | Glu | Ile | Lys | Lys | Glu | Thr |
| 1190 | | | | | 1195 | | | | 1200 | | |
| Leu | Ile | Gln | Glu | Asn | Val | Val | Leu | Pro | Gln | Ile | His | Thr | Val | Thr |
| 1205 | | | | | 1210 | | | | | 1215 | | |
| Gly | Thr | Lys | Asn | Phe | Met | Lys | Asn | Leu | Phe | Leu | Leu | Ser | Thr | Arg |
| 1220 | | | | | 1225 | | | | | 1230 | | |
| Gln | Asn | Val | Glu | Gly | Ser | Tyr | Glu | Gly | Ala | Tyr | Ala | Pro | Val | Leu |
| 1235 | | | | | 1240 | | | | | 1245 | | |
| Gln | Asp | Phe | Arg | Ser | Leu | Asn | Asp | Ser | Thr | Asn | Arg | Thr | Lys | Lys |
| 1250 | | | | | 1255 | | | | | 1260 | | |
| His | Thr | Ala | His | Phe | Ser | Lys | Lys | Gly | Glu | Glu | Glu | Asn | Leu | Glu |
| 1265 | | | | | 1270 | | | | | 1275 | | |
| Gly | Leu | Gly | Asn | Gln | Thr | Lys | Gln | Ile | Val | Glu | Lys | Tyr | Ala | Cys |
| 1280 | | | | | 1285 | | | | | 1290 | | |
| Thr | Thr | Arg | Ile | Ser | Pro | Asn | Thr | Ser | Gln | Gln | Asn | Phe | Val | Thr |
| 1295 | | | | | 1300 | | | | | 1305 | | |
| Gln | Arg | Ser | Lys | Arg | Ala | Leu | Lys | Gln | Phe | Arg | Leu | Pro | Leu | Glu |
| 1310 | | | | | 1315 | | | | | 1320 | | |
| Glu | Thr | Glu | Leu | Glu | Lys | Arg | Ile | Ile | Val | Asp | Asp | Thr | Ser | Thr |
| 1325 | | | | | 1330 | | | | | 1335 | | |
| Gln | Trp | Ser | Lys | Asn | Met | Lys | His | Leu | Thr | Pro | Ser | Thr | Leu | Thr |
| 1340 | | | | | 1345 | | | | | 1350 | | |
| Gln | Ile | Asp | Tyr | Asn | Glu | Lys | Glu | Lys | Gly | Ala | Ile | Thr | Gln | Ser |
| 1355 | | | | | 1360 | | | | | 1365 | | |
| Pro | Leu | Ser | Asp | Cys | Leu | Thr | Arg | Ser | His | Ser | Ile | Pro | Gln | Ala |
| 1370 | | | | | 1375 | | | | | 1380 | | |
| Asn | Arg | Ser | Pro | Leu | Pro | Ile | Ala | Lys | Val | Ser | Ser | Phe | Pro | Ser |
| 1385 | | | | | 1390 | | | | | 1395 | | |
| Ile | Arg | Pro | Ile | Tyr | Leu | Thr | Arg | Val | Leu | Phe | Gln | Asp | Asn | Ser |
| 1400 | | | | | 1405 | | | | | 1410 | | |
| Ser | His | Leu | Pro | Ala | Ala | Ser | Tyr | Arg | Lys | Lys | Asp | Ser | Gly | Val |
| 1415 | | | | | 1420 | | | | | 1425 | | |
| Gln | Glu | Ser | Ser | His | Phe | Leu | Gln | Gly | Ala | Lys | Lys | Asn | Asn | Leu |
| 1430 | | | | | 1435 | | | | | 1440 | | |
| Ser | Leu | Ala | Ile | Leu | Thr | Leu | Glu | Met | Thr | Gly | Asp | Gln | Arg | Glu |
| 1445 | | | | | 1450 | | | | | 1455 | | |
| Val | Gly | Ser | Leu | Gly | Thr | Ser | Ala | Thr | Asn | Ser | Val | Thr | Tyr | Lys |
| 1460 | | | | | 1465 | | | | | 1470 | | |
| Lys | Val | Glu | Asn | Thr | Val | Leu | Pro | Lys | Pro | Asp | Leu | Pro | Lys | Thr |
| 1475 | | | | | 1480 | | | | | 1485 | | |
| Ser | Gly | Lys | Val | Glu | Leu | Leu | Pro | Lys | Val | His | Ile | Tyr | Gln | Lys |
| 1490 | | | | | 1495 | | | | | 1500 | | |
| Asp | Leu | Phe | Pro | Thr | Glu | Thr | Ser | Asn | Gly | Ser | Pro | Gly | His | Leu |
| 1505 | | | | | 1510 | | | | | 1515 | | |
| Asp | Leu | Val | Glu | Gly | Ser | Leu | Leu | Gln | Gly | Thr | Glu | Gly | Ala | Ile |
| 1520 | | | | | 1525 | | | | | 1530 | | |
| Lys | Trp | Asn | Glu | Ala | Asn | Arg | Pro | Gly | Lys | Val | Pro | Phe | Leu | Arg |
| 1535 | | | | | 1540 | | | | | 1545 | | |
| Val | Ala | Thr | Glu | Ser | Ser | Ala | Lys | Thr | Pro | Ser | Lys | Leu | Leu | Asp |
| 1550 | | | | | 1555 | | | | | 1560 | | |
| Pro | Leu | Ala | Trp | Asp | Asn | His | Tyr | Gly | Thr | Gln | Ile | Pro | Lys | Glu |
| 1565 | | | | | 1570 | | | | | 1575 | | |
| Glu | Trp | Lys | Ser | Gln | Glu | Lys | Ser | Pro | Glu | Lys | Thr | Ala | Phe | Lys |

-continued

```
                1580                1585                1590
Lys Lys Asp Thr Ile Leu Ser Leu Asn Ala Cys Glu Ser Asn His
    1595                1600                1605
Ala Ile Ala Ala Ile Asn Glu Gly Gln Asn Lys Pro Glu Ile Glu
    1610                1615                1620
Val Thr Trp Ala Lys Gln Gly Arg Thr Glu Arg Leu Cys Ser Gln
    1625                1630                1635
Asn Pro Pro Val Leu Lys Arg His Gln Arg Glu Ile Thr Arg Thr
    1640                1645                1650
Thr Leu Gln Ser Asp Gln Glu Glu Ile Asp Tyr Asp Asp Thr Ile
    1655                1660                1665
Ser Val Glu Met Lys Lys Glu Asp Phe Asp Ile Tyr Asp Glu Asp
    1670                1675                1680
Glu Asn Gln Ser Pro Arg Ser Phe Gln Lys Lys Thr Arg His Tyr
    1685                1690                1695
Phe Ile Ala Ala Val Glu Arg Leu Trp Asp Tyr Gly Met Ser Ser
    1700                1705                1710
Ser Pro His Val Leu Arg Asn Arg Ala Gln Ser Gly Ser Val Pro
    1715                1720                1725
Gln Phe Lys Lys Val Val Phe Gln Glu Phe Thr Asp Gly Ser Phe
    1730                1735                1740
Thr Gln Pro Leu Tyr Arg Gly Glu Leu Asn Glu His Leu Gly Leu
    1745                1750                1755
Leu Gly Pro Tyr Ile Arg Ala Glu Val Glu Asp Asn Ile Met Val
    1760                1765                1770
Thr Phe Arg Asn Gln Ala Ser Arg Pro Tyr Ser Phe Tyr Ser Ser
    1775                1780                1785
Leu Ile Ser Tyr Glu Glu Asp Gln Arg Gln Gly Ala Glu Pro Arg
    1790                1795                1800
Lys Asn Phe Val Lys Pro Asn Glu Thr Lys Thr Tyr Phe Trp Lys
    1805                1810                1815
Val Gln His His Met Ala Pro Thr Lys Asp Glu Phe Asp Cys Lys
    1820                1825                1830
Ala Trp Ala Tyr Phe Ser Asp Val Asp Leu Glu Lys Asp Val His
    1835                1840                1845
Ser Gly Leu Ile Gly Pro Leu Leu Val Cys His Thr Asn Thr Leu
    1850                1855                1860
Asn Pro Ala His Gly Arg Gln Val Thr Val Gln Glu Phe Ala Leu
    1865                1870                1875
Phe Phe Thr Ile Phe Asp Glu Thr Lys Ser Trp Tyr Phe Thr Glu
    1880                1885                1890
Asn Met Glu Arg Asn Cys Arg Ala Pro Cys Asn Ile Gln Met Glu
    1895                1900                1905
Asp Pro Thr Phe Lys Glu Asn Tyr Arg Phe His Ala Ile Asn Gly
    1910                1915                1920
Tyr Ile Met Asp Thr Leu Pro Gly Leu Val Met Ala Gln Asp Gln
    1925                1930                1935
Arg Ile Arg Trp Tyr Leu Leu Ser Met Gly Ser Asn Glu Asn Ile
    1940                1945                1950
His Ser Ile His Phe Ser Gly His Val Phe Thr Val Arg Lys Lys
    1955                1960                1965
Glu Glu Tyr Lys Met Ala Leu Tyr Asn Leu Tyr Pro Gly Val Phe
    1970                1975                1980
```

-continued

Glu Thr Val Glu Met Leu Pro Ser Lys Ala Gly Ile Trp Arg Val
    1985                1990                1995
Glu Cys Leu Ile Gly Glu His Leu His Ala Gly Met Ser Thr Leu
    2000                2005                2010
Phe Leu Val Tyr Ser Asn Lys Cys Gln Thr Pro Leu Gly Met Ala
    2015                2020                2025
Ser Gly His Ile Arg Asp Phe Gln Ile Thr Ala Ser Gly Gln Tyr
    2030                2035                2040
Gly Gln Trp Ala Pro Lys Leu Ala Arg Leu His Tyr Ser Gly Ser
    2045                2050                2055
Ile Asn Ala Trp Ser Thr Lys Glu Pro Phe Ser Trp Ile Lys Val
    2060                2065                2070
Asp Leu Leu Ala Pro Met Ile Ile His Gly Ile Lys Thr Gln Gly
    2075                2080                2085
Ala Arg Gln Lys Phe Ser Ser Leu Tyr Ile Ser Gln Phe Ile Ile
    2090                2095                2100
Met Tyr Ser Leu Asp Gly Lys Lys Trp Gln Thr Tyr Arg Gly Asn
    2105                2110                2115
Ser Thr Gly Thr Leu Met Val Phe Phe Gly Asn Val Asp Ser Ser
    2120                2125                2130
Gly Ile Lys His Asn Ile Phe Asn Pro Pro Ile Ile Ala Arg Tyr
    2135                2140                2145
Ile Arg Leu His Pro Thr His Tyr Ser Ile Arg Ser Thr Leu Arg
    2150                2155                2160
Met Glu Leu Met Gly Cys Asp Leu Asn Ser Cys Ser Met Pro Leu
    2165                2170                2175
Gly Met Glu Ser Lys Ala Ile Ser Asp Ala Gln Ile Thr Ala Ser
    2180                2185                2190
Ser Tyr Phe Thr Asn Met Phe Ala Thr Trp Ser Pro Ser Lys Ala
    2195                2200                2205
Arg Leu His Leu Gln Gly Arg Ser Asn Ala Trp Arg Pro Gln Val
    2210                2215                2220
Asn Asn Pro Lys Glu Trp Leu Gln Val Asp Phe Gln Lys Thr Met
    2225                2230                2235
Lys Val Thr Gly Val Thr Thr Gln Gly Val Lys Ser Leu Leu Thr
    2240                2245                2250
Ser Met Tyr Val Lys Glu Phe Leu Ile Ser Ser Ser Gln Asp Gly
    2255                2260                2265
His Gln Trp Thr Leu Phe Phe Gln Asn Gly Lys Val Lys Val Phe
    2270                2275                2280
Gln Gly Asn Gln Asp Ser Phe Thr Pro Val Val Asn Ser Leu Asp
    2285                2290                2295
Pro Pro Leu Leu Thr Arg Tyr Leu Arg Ile His Pro Gln Ser Trp
    2300                2305                2310
Val His Gln Ile Ala Leu Arg Met Glu Val Leu Gly Cys Glu Ala
    2315                2320                2325
Gln Asp Leu Tyr
    2330

<210> SEQ ID NO 2
<211> LENGTH: 22
<212> TYPE: DNA
<213> ORGANISM: artificial
<220> FEATURE:

<223> OTHER INFORMATION: FVIII Specific Primer

<400> SEQUENCE: 2
agcacaaagg tagaaggcaa gc                                22

<210> SEQ ID NO 3
<211> LENGTH: 22
<212> TYPE: DNA
<213> ORGANISM: artificial
<220> FEATURE:
<223> OTHER INFORMATION: FVIII Specific Primer

<400> SEQUENCE: 3 cctttttgctt ctccagttga ac                               22

<210> SEQ ID NO 4
<211> LENGTH: 22
<212> TYPE: DNA
<213> ORGANISM: artificial
<220> FEATURE:
<223> OTHER INFORMATION: FVIII Specific Primer

<400> SEQUENCE: 4
ttctctgtga ggtaccagct tc                                22

<210> SEQ ID NO 5
<211> LENGTH: 22
<212> TYPE: DNA
<213> ORGANISM: artificial
<220> FEATURE:
<223> OTHER INFORMATION: FVIII Specific Primer

<400> SEQUENCE: 5
tgcctgaccc gctattactc ta                                22

<210> SEQ ID NO 6
<211> LENGTH: 22
<212> TYPE: DNA
<213> ORGANISM: artificial
<220> FEATURE:
<223> OTHER INFORMATION: FVIII Specific Primer

<400> SEQUENCE: 6
tctatctgtg tgagggtgct cg                                22

<210> SEQ ID NO 7
<211> LENGTH: 22
<212> TYPE: DNA
<213> ORGANISM: artificial
<220> FEATURE:
<223> OTHER INFORMATION: FVIII Specific Primer

<400> SEQUENCE: 7
ggaggaagaa aacttggaag gc                                22

<210> SEQ ID NO 8
<211> LENGTH: 38
<212> TYPE: DNA
<213> ORGANISM: artificial
<220> FEATURE:
<223> OTHER INFORMATION: FVIII deletion primer

<400> SEQUENCE: 8
cttctcccag aattcaagac aagaggaaat tgactatg               38

```
<210> SEQ ID NO 9
<211> LENGTH: 37
<212> TYPE: DNA
<213> ORGANISM: artificial
<220> FEATURE:
<223> OTHER INFORMATION: FVIII deletion primer

<400> SEQUENCE: 9
cctagcacta ggcaaaagca agaggaaatt gactatg                              37

<210> SEQ ID NO 10
<211> LENGTH: 40
<212> TYPE: DNA
<213> ORGANISM: artificial
<220> FEATURE:
<223> OTHER INFORMATION: FVIII deletion primer

<400> SEQUENCE: 10
caatttaatg ccaccacaat tcaagaggaa attgactatg                           40

<210> SEQ ID NO 11
<211> LENGTH: 39
<212> TYPE: DNA
<213> ORGANISM: artificial
<220> FEATURE:
<223> OTHER INFORMATION: FVIII deletion primer

<400> SEQUENCE: 11
cagaaaatga catagagaag caagaggaaa ttgactatg                            39

<210> SEQ ID NO 12
<211> LENGTH: 37
<212> TYPE: DNA
<213> ORGANISM: artificial
<220> FEATURE:
<223> OTHER INFORMATION: FVIII deletion primer

<400> SEQUENCE: 12
gacccttggt ttgcacacca agaggaaatt gactatg                              37

<210> SEQ ID NO 13
<211> LENGTH: 54
<212> TYPE: DNA
<213> ORGANISM: artificial
<220> FEATURE:
<223> OTHER INFORMATION: FVIII deletion primer

<400> SEQUENCE: 13
gcacacagaa cacctatgcc taaaatacaa gaggaaattg actatgatga tacc           54

<210> SEQ ID NO 14
<211> LENGTH: 27
<212> TYPE: DNA
<213> ORGANISM: artificial
<220> FEATURE:
<223> OTHER INFORMATION: FVIII mutagentic primer

<400> SEQUENCE: 14
cgtgatccat gtcgacgcct gcttgcc                                         27

<210> SEQ ID NO 15
<211> LENGTH: 39
<212> TYPE: DNA
<213> ORGANISM: artificial
<220> FEATURE:
<223> OTHER INFORMATION: FVIII mutagenic primer
```

-continued

```
<400> SEQUENCE: 15
caagaagctt ctcccagaaa ataactcgta ctactcttc                    39

<210> SEQ ID NO 16
<211> LENGTH: 38
<212> TYPE: DNA
<213> ORGANISM: artificial
<220> FEATURE:
<223> OTHER INFORMATION: FVIII mutagenic primer

<400> SEQUENCE: 16
caagaagctt ctcccagaaa actactcttc agtcagtc                     38

<210> SEQ ID NO 17
<211> LENGTH: 42
<212> TYPE: DNA
<213> ORGANISM: artificial
<220> FEATURE:
<223> OTHER INFORMATION: FVIII mutagenic primer

<400> SEQUENCE: 17
caagaagctt ctcccagaaa cagtcagatc aagaggaaat tg                42

<210> SEQ ID NO 18
<211> LENGTH: 39
<212> TYPE: DNA
<213> ORGANISM: artificial
<220> FEATURE:
<223> OTHER INFORMATION: FVIII mutagenic primer

<400> SEQUENCE: 18
ctaggcaaaa gcaatttaat ataactcgta ctactcttc                    39

<210> SEQ ID NO 19
<211> LENGTH: 38
<212> TYPE: DNA
<213> ORGANISM: artificial
<220> FEATURE:
<223> OTHER INFORMATION: FVIII mutagenic primer

<400> SEQUENCE: 19
ctaggcaaaa gcaatttaat actactcttc agtcagtc                     38

<210> SEQ ID NO 20
<211> LENGTH: 42
<212> TYPE: DNA
<213> ORGANISM: artificial
<220> FEATURE:
<223> OTHER INFORMATION: FVIII mutagenic primer

<400> SEQUENCE: 20
ctaggcaaaa gcaatttaat cagtcagatc aagaggaaat tg                42

<210> SEQ ID NO 21
<211> LENGTH: 38
<212> TYPE: DNA
<213> ORGANISM: artificial
<220> FEATURE:
<223> OTHER INFORMATION: FVIII mutagenic primer

<400> SEQUENCE: 21
caccacaatt ccagaaaata taactcgtac tactcttc                     38

<210> SEQ ID NO 22
<211> LENGTH: 37
```

```
<212> TYPE: DNA
<213> ORGANISM: artificial
<220> FEATURE:
<223> OTHER INFORMATION: FVIII mutagenic primer

<400> SEQUENCE: 22
caccacaatt ccagaaaata ctactcttca gtcagtc                                    37

<210> SEQ ID NO 23
<211> LENGTH: 41
<212> TYPE: DNA
<213> ORGANISM: artificial
<220> FEATURE:
<223> OTHER INFORMATION: FVIII mutagenic primer

<400> SEQUENCE: 23
caccacaatt ccagaaaatc agtcagatca agaggaaatt g                               41

<210> SEQ ID NO 24
<211> LENGTH: 27
<212> TYPE: DNA
<213> ORGANISM: artificial
<220> FEATURE:
<223> OTHER INFORMATION: FVIII mutagenic primer

<400> SEQUENCE: 24
cgtgatccat gtcgacgcct gcttgcc                                               27

<210> SEQ ID NO 25
<211> LENGTH: 33
<212> TYPE: DNA
<213> ORGANISM: artificial
<220> FEATURE:
<223> OTHER INFORMATION: FVIII mutagenic primer

<400> SEQUENCE: 25
aacaatgcca ttgaattcag aagcttctcc cag                                        33
```

FACTOR VIII POLYPEPTIDE

BACKGROUND OF THE INVENTION

1. Field of the Invention

The present invention relates to Factor VIII polypeptides that are more stable than full-length Factor VIII. The present invention also relates to a method of administering the Factor VIII polypeptide to a subject to treat a blood disorder. The invention further relates to a nucleic acid construct including DNA encoding the Factor VIII polypeptide. The invention relates to a method of expressing Factor VIII in a mammal by administering the gene construct to the subject. The invention is further related to antibodies specific for the Factor VIII polypeptide.

2. General Background and State of the Art

Hemophilia A results from the quantitative or qualitative deficiency of Factor VIII (FVIII), necessitating exogenous replacement by either plasma- or recombinant-derived FVIII preparations. FVIII has a domain organization of A1-A2-B-A3-C1-C2 and is synthesized as a 2,351-amino acid single-chain glycoprotein of 280 kDa (Eaton, D. et al., 1986, *Biochenlistly* 25: 505–512; Toole, J. J. et al., 1984, *Nature* 312: 342; Vehar, G. A. et al., 1984, *Nature* 312: 337). Whereas the A and C domains exhibit 35–40% amino acid identity to each other and to the A and C domains of coagulation factor V, the B domain is not homologous to any known protein. Intracellular, proteolytic processing after residue Arg-1648 within the B domain generates an 80-kDa light chain (domains A3-C1-C2) and a heterogeneous-sized heavy chain of 90–200 kDa (domains A1-A2-B). The heavy and light chains are associated as a heterodimer through a divalent metal-ion-dependent linkage between the A1 and A3 domains. In plasma, FVIII circulates in an inactive form bound to von Willebrand factor (vWF) and requires proteolytic cleavage by thrombin or Factor Xa for activation (Eaton, D., et al., 1986, *Biochelnistiy* 25: 505–512; Girma, J. P. et al., 1987, *Blood* 70: 605–611; Koedam, J. A. et al., 1990, *Eur. J. Biocheln*. 189: 229–234). Thrombin cleavage after Arg (R) residues 372, 740, and 1689 activates FVIII coagulant activity, resulting in the complete removal of the B domain. The resulting FVIIIa heterotrimer retains the metal ion-dependent linkage between the A1 and A3-C1-C2 subunits, whereas A2 is associated with a weak affinity by electrostatic interactions (Eaton, D. et al., 1986, *Biochemistiy* 25: 505–512; Fay, P. J. et al., 1991, *J. Biol. Chem*. 266: 8957–8962; Pittman, D. D. & Kaufinan, R. J. 1988, *Proc. Natl. Acad. Sci. USA* 85: 2429–2433).

With an increased understanding of the biosynthesis, structure, and function of FVIII, studies have attempted to produce improved FVIII molecules for replacement therapy for patients with hemophilia A. Strategies investigated thus far have included the deletion or modification of FVIII sequences, resulting in more efficient expression. Previous studies on the requirements for functional activity of FVIII demonstrated that cleavage after Arg residues 372 and 1689 both were required for activation of FVIII and that the B domain was not required for functional activity (Eaton, D. L. et al., 1986, *Biochemistty* 25: 8343; Burke, R. L. et al., 1986, *J. Biol. Chem* 261: 12574; Toole, J. J. et al., 1986, *Proc. Natl. Acad. Sci*. USA 83: 5939). In order to test this hypothesis, several approaches such as the deletion, in the complementary DNA (cDNA), of large DNA fragments corresponding to domain B, giving shorter FVIII derivatives (Eaton, D. L. et al., 1986, *Biocheinistry* 25: 8343; Burke, R. L. et al., 1986, *J Biol. Chem* 261: 12574) were conducted and tested for their coagulation activity.

PCT application WO 86/06101 discloses that recombinant FVIII proteins with deletions of up to 880 amino acids in the central region still exhibit FVIII activity. In addition, Eaton et al., 1986, *Biochemistoy* 25:8343–8347, disclose that a polypeptide in which 766 amino acids (797 through 1562) have been deleted from the central B domain region also retains FVIII activity. These B-domain-deleted FVIII derivatives retained a site for intracellular proteolytic processing within the B domain after residue Arg-1648, which results in generation of heterogenous FVIII derivatives comprising single chain or a complex of two proteolytic cleavage products of FVIII, a 90 kDa (domains A1-A2) and an 80 kDa (domains A3-C1-C2) polypeptide. Moreover, mammalian cells transformed with a vector containing DNA encoding this deletion polypeptide had a higher production level than cells transformed with a vector containing DNA encoding the full length polypeptide. However, these B-domain deleted FVIII derivatives exhibit faster and higher activation rates by thrombin than full-length FVIII by unknown mechanisms (Eaton et al., 1986, *Biochemistry* 25:8343–8347; Fay et al., 1986, *Biochem. Biophys. Acta* 871:268–278).

U.S. Pat. No. 5,112,950 describes a FVIII derivative in which a human FVIII derivative consisting essentially of the amino acid sequence alanine-1 through aspartate-770 is linked to threonine-1667 through tyrosine-2332, wherein aspartate-770 is covalently bonded by a peptide bond to threonine-1667. A number of studies indicate that tyrosine residues at positions 346, 718, 719, 723, 1664, and 1680 are required for full activation and procoagulant activity of FVIII (Donath M. J. et al., 1995, *Biochem. J* 312: 49–55; Michnick D. A. et al., 1994, *J Biol. Chem*. 269:20095–200102). FVIII circulating in the plasma is combined with vWF, which appears to stabilize it; in effect, the half-life of FVIII in vivo decreases very rapidly in the absence of vWF (Brinkhous, K. M. et al., 1985, *Proc. Natl. Acad. Sci. USA* 82: 8752–8756). These studies strongly suggest that B-domain deleted Factor VIII analogs (described in U.S. Pat. No. 5,112,950, in particular), with structural alterations around 1664–1680 in the A3 region, may have potential drawbacks in terms of full activation and in vivo stability due to interference with vWF interaction. As described in U.S. Pat. No. 5,610,278, the co-expression of heavy and light chains in mammalian cells results in detectable production of FVIII. However, the combination of the two chains is inefficient, thereby decreasing the activity of the molecule (Burke, R. L. et al., 1986, *J. Biol. Chem*. 261, 12574; Pavirani A. et al., 1987, *Biochem Biophys Res Commun*. 145:234). The strategy of coexpression of heavy and light chains as a gene therapy approach in animals or humans is found to be inappropriate (Burton M et al., 1999, *Proc Natl Acad Sci USA* 96:12725).

U.S. Pat. Nos. 5,422,260 and 5,451,521 relate to variants of FVIII, wherein one or more of the Factor Xa, APC and thrombin cleavage sites are modified to render such sites less labile to specific proteolysis, for example, wherein one or both of the amino acids defining the cleavage site, preferably at least the arginine residues at R-740 or R-1648, is replaced by a different amino acid; and wherein the protein with deletion of amino acids from S-741 through R-1648 (fusing R-740 of the 90 kD site to E-1649 of the 80 kD site) is described but its coagulation activity was not revealed. The potential disadvantage of this modification at cleavage sites with a different amino acid is that the resultant protein would have a new epitope to potentially provoke an immunologic response. In addition, the references do not provide specified variants with internal deletion of amino acids between R-740 and R-1689 except for the one having internal deletion of amino acids from S-741 through R-1648.

Recent studies (Chiang GG et al., 1999, *Human Gene Therapy* 10: 61–76) show that the B-domain deleted FVIII that is generated by deletion of amino acids from S-743 through R-1648 (fusing F-742 of N-terminal of B domain to E-1649 of the 80 kD site) which is similar to the one described in U.S. Pat. Nos. 5,422,260 and 5,451,521 exhibited only ~50% biological activity and less specific activity and was therefore considered less suitable for therapeutic application. The reason why such a B-domain deleted FVIII possesses less biological and specific activity remains unknown. However, it is assumed that the nature of single chain FVIII with a deletion of amino acids from S-743 through R-1648 may have a different tertiary structural configuration probably due to the absence of spatial requirements between heavy chain (A1-A2) and light chain (A3-C1-C2) or to undesirable length or composition between heavy chain (A1-A2) and light chain (A3-C1-C2).

In summary, these previous strategies, although offering potential for more efficient manufacturing of recombinant protein, have not been successful. This lack of success is possibly due to their molecular characteristics such as heterogenous population of FVIII molecules, structural instability, and different thrombin activation profiles compared with that of full-length FVIII. In addition, since a variety of B-domain deleted FVIII are expressed as fused molecules, there is a possibility that the unnatural amino acid sequence (junction region of heavy chain and light chain) will remain without complete processing, and when administered into blood, possibly show a novel antigenicity (Esmon P. C., et al., 1990, *Blood* 76: 1593–1600, 1990). However, it is not clear whether the unnatural amino acid sequences in the fusion sites could be immunogenic, as demonstrated by the previous study (Pittman D. D. et al., 1993, *Blood* 81:2925). Under the circumstances, there is a desire for the development of an active and safe FVIII derivative that possesses similar profiles of thrombin activation and improved productivity.

SUMMARY OF THE INVENTION

The present inventors have intensively studied the structural functional relationship of FVIII derivatives so as to develop stable and efficiently expressed forms of human FVIII which contains essential components including a heavy chain, a polypeptide spacing linker, and a light chain. As a result, in one aspect, we have found the FVIII derivatives in which a major part of the B-domain is deleted and heavy chain (A1-A2) and light chain (A3-C1-C2) are linked by a polypeptide spacer of optimal composition and length (up to about 60 amino acids originated from N-terminal regions of B and A3 domains of the natural form of human Factor VIII). The FVIII derivatives of this invention are expressed mostly in a single chain of B-domain deleted FVIII by fusion of N-terminal sequence of B-domain to the amino acid sequence in A3 beyond Arg-1648. Some of these FVIII derivatives have full coagulation activity, higher specific activity, and similar thrombin activation profiles compared with full-length FVIII under the same circumstances. In addition, to prevent exposure of a new epitope of unnatural amino acid sequence in the junction region of heavy chain and light chain, we created an N-glycosylation recognition sequence (Asn-X-Ser/Thr where X can be any amino acid) in the fusion sites. This was accomplished by linking Asn in the positions of 745, 757 and 764 to amino acids in the positions of 1650, 1653 and 1656 located next to Ser or Thr amino acids in the positions of 1651, 1654, and 1657, which generate a N-linked glycosylation site in the fusion sites. In addition, this invention provides B-domain deleted FVIII derivatives containing modifications at 739 proline relative to the natural FVIII which reduces the lability of the molecules for specific protease-catalyzed cleavage at the 740 cleavage site. However, FVIII derivatives of this invention can still be activated by thrombin and still possesses procoagulant activity.

The present invention is directed to a Factor VIII polypeptide comprising an internal deletion of one or more amino acids between 1649 and 1688 fused to any amino acid sequence in the B domain from about 741 to 782, with reference to full-length human Factor VIII amino acid sequence (SEQ ID NO:1). The Factor VIII polypeptide may contain internal deletion in amino acids 746 to 1649, 746 to 1652, 746 to 1655, 758 to 1649, 758 to 1652, 758 to 1655, 765 to 1649, 765 to 1652, 765 to 1655, 748 to 1658, 755 to 1658, 762 to 1658, 769 to 1658, 776 to 1658, or 783 to 1658. The Factor VIII polypeptide may be a single chain. In addition, in another embodiment, proline at position 739 may be replaced by another amino acid.

In another aspect of the invention, the Factor VIII polypeptide of the invention may have introduced into it a tripeptide sequence (Asn-X-Thr or Asn-X-Ser) encompassing fusion sites between Asn amino acid at positions 745, 757, or 764, and Thr or Ser amino acid at positions 1651, 1654, or 1657, with reference to full-length human Factor VIII amino acid sequence (SEQ ID NO:1).

The present invention is also directed to a Factor VIII polypeptide represented by following formula with the following linked domains:

H-S-L wherein

H domain represents a polypeptide sequence comprising substantially Ala-1 through Arg-740 of human Factor VIII according to SEQ ID NO:1;

S domain represents a polypeptide spacing linker comprising up to about 60 amino acids, wherein the N-terminal end of the S domain is about residue 740, and the C-terminal of the S domain ends at about residue 1688 of human Factor VIII according to SEQ ID NO:1; and L domain represents a polypeptide sequence, which comprises substantially Arg-1689 through Tyr-2332 of human Factor VIII according to SEQ ID NO:1.

The invention is also directed to a Factor VIII polypeptide according to the above, wherein the S domain comprises amino acid sequence, which is substantially similar to a consecutive sequence from about Ser-741 through Asn-745, Arg-747, Lys-754, Asn-757, Ile-761, Asn-764, Lys-768, His-775, or Ile-782. In another embodiment, in the Factor VIII polypeptide above, the S domain comprises amino acid sequence substantially similar to a consecutive sequence from about Glu-1649 through Pro-1688. In another aspect of the invention, the S domain may comprise amino acid sequence substantially similar to a consecutive sequence from about Ile-1650, Thr-1653, Gln-1656 or Gln-1659, through Pro-1688. In another aspect of the invention, in the S domain, amino acids 746 to 1649, 746 to 1652, 746 to 1655, 758 to 1649, 758 to 1652, 758 to 1655, 765 to 1649, 765 to 1652, 765 to 1655, 748 to 1658, 755 to 1658, 762 to 1658, 769 to 1658, 776 to 783 to 1658 may be deleted, wherein the residue numbers are with reference to SEQ ID NO:1.

The invention is directed to a pharmaceutical composition comprising the Factor VIII polypeptide described above and a pharmaceutically acceptable carrier thereof. The invention is also directed to a lyophilized composition comprising the above-described Factor VIII polypeptide.

The invention is also directed to a method of clotting blood in a subject, comprising contacting a clotting effective amount of the Factor VIII polypeptide described above. The invention is further directed to a method of treating Hemophilia A in a patient, comprising administering a clotting effective amount of the Factor VIII polypeptide described above to a person in need thereof.

The invention is directed to an isolated nucleic acid encoding the Factor VIII polypeptide described above. Further, the invention is directed to an expression vector comprising the nucleic acid encoding the Factor VIII polypeptide described above, operably linked to a promoter. And further, the invention is directed to a host cell comprising the expression vector. Related to this, the invention is directed to a method of making the Factor VIII polypeptide described above, comprising culturing the cell in conditions suitable for the vector to express the polypeptide, and isolating the polypeptide.

The invention is directed to a method of clotting blood in a subject comprising:

a) generating a recombinant viral or plasmid vector comprising a nucleic acid sequence encoding the Factor VIII polypeptide described above;

b) transfecting in vitro a population of cultured cells with said recombinant vector, resulting in a population of transfected cells; and c) administering the cells to a mammalian host, such that expression of said nucleic acid sequence within said host results in clotting of blood.

The invention is also directed to a purified antibody specific for the Factor VIII polypeptide described above.

These and other objects of the invention will be more fully understood from the following description of the invention, the referenced drawings attached hereto and the claims appended hereto.

DESCRIPTION OF THE DRAWINGS

The present invention will become more fully understood from the detailed description given herein below, and the accompanying drawings which are given by way of illustration only, and thus are not limitative of the present invention, and wherein;

FIGS. 1A and 1B show the amino acid sequence of full-length FVIII.

FIG. 5A—stable transfected HEK293 cells were pulse-labeled with [$^{35}$S]methionine for 30 min. Duplicate labeled cells were chased for 6 hr in medium containing excess unlabeled methionine, and then cell extracts (C) and conditioned medium (M) were harvested. Equal volumes of cell extract and conditioned medium were immunoprecipated with anti-FVIII-specific antibody, and equal aliquots were analyzed by SDS/PAGE. All of the derivatives were recovered from cell extracts (lanes 3, 5, 7, 9, 11, 13, 15, and 17) and the chase-conditioned medium (lanes 4, 6, 8, 10, 12, 14, 16, and 18) as single-chain species. HEK293 indicates HEK293 cells that did not possess exogenous DNA plasmid DNA.

FIG. 5B—HEK293 cell lines expressing FVIII derivatives were grown in DMEM supplemented with 10% fetal bovine serum and antibiotics. When monolayer grew to around 70–80% confluence, culture media was replaced with fresh DMEM. Cells were incubated for about 24 hrs and culture supernatant was harvested, concentrated approximately 100-fold using Centricon 50,000 MWCO, and stored at −80° C. FVIII concentration was measured using ELISA method. Concentrates were then separated by SDS-PAGE and analyzed by immunoblotting using a monoclonal antibody (ESH-8). ESH-8 antibody used in Western blotting detected a major protein, migrating to approximately 170 kDa (indicated by arrow).

FIG. 5C—$^{35}$S-methionine labeled FVIII derivatives were immunoprecipitated from the chase conditioned medium of stably expressing HEK293 cells, and were divided into equal aliquots and incubated in the absence (lanes 1, 3, 5, and 7) or presence (lanes 2, 4, 6, and 8) of thrombin (1 U/mL) for 30 min at 37° C. Reactions were terminated with SDS-PAGE sample buffer and protein fragments were separated by 10% SDS-PAGE. FVIII protein forms are indicated at the right as follows: SC, single chain; A1, and A2, thrombin-cleaved heavy chain fragments; LC, thrombin-cleaved light chain. Analysis of the radiolabeled protein after thrombin digestion indicated a normal appearance of the 73 kD, and 50 and 40 kD fragments corresponding to the molecular sizes of thrombin-cleaved light chain, A1 and A2 domains, respectively. The names of each FVIII derivatives are indicated on the top. Molecular mass markers are shown on the left of each image.

FIG. 7A shows thrombin activation kinetics for recombinant human FVIII (rh FVIII), dB761, dB782, dB761–739F, and dB782–739F. FIG. 7B shows thrombin activation kinetics for recombinant human FVIII (rh FVIII), dBN(57-50), dBN(45-53), dBN(57-56), dBN(64-50), dBN (64-53), and dBN(64-56).

DETAILED DESCRIPTION OF THE PREFERRED EMBODIMENTS

Figure 2:
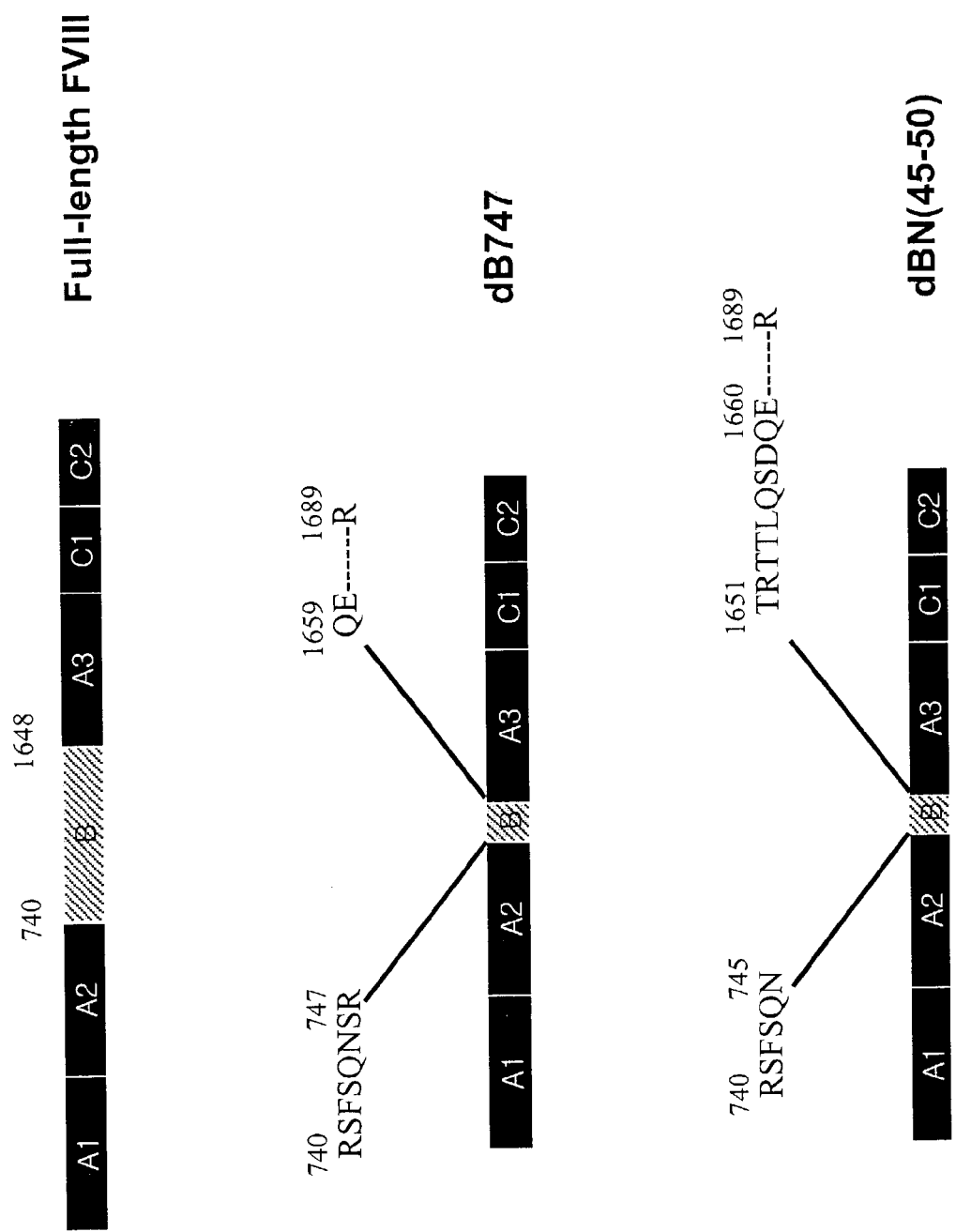
FIG. 2 shows a schematic representation of the full-length FVIII and various B-domain deleted FVIII derivatives dB747 and dBN(45–50).

In the present application, "a" and "an" are used to refer to both single and a plurality of objects.

As used herein, "about" or "substantially" generally provides leeway from being limited to an exact number. For example, as used in the context of the length or position of a polypeptide sequence, "about" or "substantially" indicates that the polypeptide is not to be limited to the exact recited number or position as that which is indicated, so long as the function and result achieved is the same. A few amino acid positions may be inserted, deleted, or added or deleted from the N- or C-terminal ends so long as the functional activity ascribed to such amino acid positions, such as thrombin cleavage and protease cleavage functions are either maintained or inactivated through deletion or mutation of the various amino acids pertaining to site of function.

Furthermore, as used herein, "substantially similar" sequence of nucleic acid or amino acid sequence refers to one having 70%, 75%, 80%, 85%, 90%, 95%, 96%, 97%, 98%, 99% or 100% sequence homology to the indicated reference sequence.

As used herein, "amino acid" and "amino acids" refer to all naturally occurring L-α-amino acids. This definition is meant to include norleucine, ornithine, and homocysteine.

As used herein, in general, the term "amino acid sequence variant" refers to molecules with some differences in their amino acid sequences as compared to a reference (e.g. native Factor VIII sequence) polypeptide. The amino acid alterations may be substitutions, insertions, deletions or any desired combinations of such changes in a native amino acid sequence.

Substitutional variants are those that have at least one amino acid residue in a native sequence removed and a different amino acid inserted in its place at the same position. The substitutions may be single, where only one amino acid in the molecule has been substituted, or they may be multiple, where two or more amino acids have been substituted in the same molecule.

Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. The polar neutral amino acids include glycine, serine, threonine, cysteine, tyrosine, asparagine and glutamine. The positively charged (basic) amino acids include arginine, lysine and histidine. The negatively charged (acidic) amino acids include aspartic acid and glutamic acid. Also included within the scope of the invention are proteins or fragments or derivatives thereof which exhibit the same or similar biological activity and derivatives which are differentially modified during or after translation, e.g., by glycosylation, proteolytic cleavage, linkage to an antibody molecule or other cellular ligand, and so on.

Insertional variants are those with one or more amino acids inserted immediately adjacent to an amino acid at a particular position in a native amino acid sequence. Immediately adjacent to an amino acid means connected to either the α-carboxy or α-amino functional group of the amino acid.

Deletional variants are those with one or more amino acids in the native amino acid sequence removed. Ordinarily, deletional variants will have one or two amino acids deleted in a particular region of the molecule.

In one aspect, the polypeptide variant of the present invention may contain any number of amino acids or alterations of amino acids in the FVIII non-critical region, including substitutions and/or insertions and/or deletions in any other region of the polypeptide molecule, so long as the polypeptide variant includes a sequence that is at least about 70%, 75%, 80%, 85%, 90%, 95%, 96%, 97%, 98% or 99% identical to about 1–740 and/or 1689–2332 polypeptide sequence of SEQ ID NO:1, and the presence of the variations do not hinder the variant FVIII activity.

The amino acid symbols used in the present application include the following:

Either single or three letter abbreviations for the amino acids are used throughout the application, and may be used interchangeably, and have the following meaning: A or Ala=alanine; R or Arg=arginine; N or Asn=asparagine; D or Asp=aspartic acid; C or Cys=cysteine; Q Gln=glutamine; E or Glu=glutamic acid; G or Gly=glycine; H or His=histidine; I or Ile=isoleucine; L or Leu=leucine; K or Lys=lysine; M or Met=methionine; F or Phe=phenylalanine; P or Pro=proline; S or Ser=serine; T or Thr=threonine; W or Trp=tryptophan; Y or Tyr=tyrosine; and V or Val=valine.

As used herein, "Factor VIII derivative", "Factor VIII variant", or "Factor VIII polypeptide" refers to a polypeptide that has coagulation activity, higher specific activity and similar thrombin activation profile compared with full-length human Factor VIII, and has at least about 70%, 75%, 80%, 85%, 90%, 95%, 96%, 97%, 98%, 99% or 100% identity to the 1–740 and 1689–2332 regions of the polypeptide sequence represented by SEQ ID NO:1. In particular, it is understood that various mutations and conservative amino acid changes are tolerable, as well as certain non-conservative amino acid changes, so long as the variant Factor VIII has coagulation activity. Fragments and certain glycosylations are also permitted, and preferred, indeed any change at all to the Factor VIII polypeptide is permitted so long as the polypeptide retains its specific activity.

Applicants for the first time discovered that Factor VIII derivatives, which has either deleted or varied B region in which the thrombin cleavage regions at 740 and 1689 are kept in tact, but much of the area between 740 and 1689 may be deleted, including 1648, without causing any negative effect on the specific activity of the variant Factor VIII. Thus, it would be within the purview of a person of skill in the art to make certain variations to the sequence, which retains the specific activity of Factor VIII.

As used herein, the term "capable of hybridizing under high stringency conditions" means annealing a strand of DNA complementary to the DNA of interest under highly stringent conditions. Likewise, "capable of hybridizing under low stringency conditions" refers to annealing a strand of DNA complementary to the DNA of interest under low stringency conditions. "High stringency conditions" for the annealing process may involve, for example, high temperature and/or low salt content, which disfavor hydrogen-bonding contacts among mismatched base pairs. "Low stringency conditions" would involve lower temperature, and/or higher salt concentration than that of high stringency conditions. Such conditions allow for two DNA strands to anneal if substantial, though not near complete complementarity exists between the two strands, as is the case among DNA strands that code for the same protein but differ in sequence due to the degeneracy of the genetic code. Appropriate stringency conditions which promote DNA hybridization, for example, 6×SSC at about 45° C., followed by a wash of 2×SSC at 50° C. are known to those skilled in the art or can be found in Current Protocols in Molecular Biology, John Wiley & Sons, N.Y. (1989), 6.31–6.3.6. For example, the salt concentration in the wash step can be selected from a low stringency of about 2×SSC at 50° C. to a high stringency of about 0.2×SSC at 50° C. In addition, the temperature in the wash step can be increased from low stringency at room temperature, about 22° C., to high stringency conditions, at about 75° C. Other stringency parameters are described in Maniatis, T., et al., Molecular Cloning: A Laboratory Manual, Cold Spring Harbor Laboratory Press, Cold Spring N,Y., (1982), at pp. 387–389; see also Sambrook J. et al., Molecular Cloning: A Laboratory Manual, Second Edition, Volume 2, Cold Spring Harbor Laboratory Press, Cold Spring, N.Y. at pp. 8.46–8.47 (1989).

As used herein, "carriers" include pharmaceutically acceptable carriers, excipients, or stabilizers which are non-toxic to the cell or mammal being exposed thereto at the dosages and concentrations employed. Often the pharmaceutically acceptable carrier is an aqueous pH buffered solution. Examples of pharmaceutically acceptable carriers include without limitation buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN®, polyethylene glycol (PEG), and PLURONICS®.

As used herein, "covalent derivatives" include modifications of the polypeptide or a fragment thereof with an organic proteinaceous or non-proteinaceous derivatizing agent, and post-translational modifications. Covalent modifications are traditionally introduced by reacting targeted amino acid residues with an organic derivatizing agent that is capable of reacting with selected sides or terminal residues, or by harnessing mechanisms of post-translational modifications that function in selected recombinant host cells. Certain post-translational modifications are the result of the action of recombinant host cells on the expressed polypeptide. Glutaminyl and asparaginyl residues are frequently post-translationally deamidated to the corresponding glutamyl and aspartyl residues. Alternatively, these residues are deamidated under mildly acidic conditions. Either form of these residues may be present in the Factor VIII polypeptides of the present invention. Other post-translational modifications include glycosylation, hydroxylation of proline and lysine, phosphorylation of hydroxyl groups of seryl, tyrosine or threonyl residues, methylation of the α-amino groups of lysine, arginine, and histidine side chains (T. E. Creighton, Proteins: Structure and Molecular Properties, W.H. Freeman & Co., San Francisco, pp. 79–86 (1983)).

As used herein, "effective amount" is an amount sufficient to effect beneficial or desired clinical or biochemical results. An effective amount can be administered one or more times. For purposes of this invention, an effective amount of an inhibitor compound is an amount that is sufficient to palliate, ameliorate, stabilize, reverse, slow or delay the progression of the disease state. In a preferred embodiment of the invention, the "effective amount" is defined as an amount of compound capable of effecting coagulation of blood.

As used herein, "fragment" refers to a part of a polypeptide, which retains usable and functional characteristics. For example, as used within the context of the present invention, the Factor VIII polypeptide fragment has the function of coagulating blood.

As used herein, "host cell" includes an individual cell or cell culture, which can be or has been a recipient of a vector of this invention. Host cells include progeny of a single host cell, and the progeny may not necessarily be completely identical (in morphology or in total DNA complement) to the original parent cell due to natural, accidental, or deliberate mutation and/or change. A host cell includes cells transfected or infected in vivo with a vector comprising a polynucleotide encoding an angiogenic factor.

As used herein, "mammal" for purposes of treatment refers to any animal classified as a mammal, including humans, domestic and farm animals, and zoo, sports, or pet animals, such as dogs, cats, cattle, horses, sheep, pigs, and so on. Preferably, the mammal is human.

As used herein, "purified" or "isolated" molecule refers to biological molecules that are removed from their natural environment and are isolated or separated and are free from other components with which they are naturally associated.

As used herein, "sample" or "biological sample" is referred to in its broadest sense, and includes any biological sample obtained from an individual, body fluid, cell line, tissue culture, or other source, In addition, a "biological sample" obtained from a patient can be referred to either as a "biological sample" or a "patient sample."

As used herein, "sequence identity", is defined as the percentage of amino acid residues in a candidate sequence that are identical with the amino acid residues in a native polypeptide sequence after aligning the sequences and introducing gaps, if necessary, to achieve the maximum percent sequence identity, and not considering any conservative substitutions as part of the sequence identity. The % sequence identity values are generated by the NCBI BLAST2.0 software as defined by Altschul et al., (1997), "Gapped BLAST and PSI-BLAST: a new generation of protein database search programs", Nucleic Acids Res., 25:3389–3402. The parameters are set to default values, with the exception of the Penalty for mismatch, which is set to −1.

As used herein, the term "specific activity" or "specific biological activity" of FVIII polypeptide refers to the quantitative measurement of functional FVIII molecules with coagulation activity present in total FVIII molecules which is represented by the ratio of FVIII coagulation activity to the amount of FVIII antigen associated with Factor VIII polypeptides. Specific activity or specific biological activity is affected by multiple factors such as the potency of coagulation activity, thrombin activation profile, structural stability, and structural conformation, compared with full-length human Factor VIII.

As used herein, "subject" is a vertebrate, preferably a mammal, more preferably a human.

As used herein, "treatment" is an approach for obtaining beneficial or desired clinical results. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. "Treatment" refers to both therapeutic treatment and prophylactic or preventative measures. Those in need of treatment include those already with the disorder as well as those in which the disorder is to be prevented. "Palliating" a disease means that the extent and/or undesirable clinical manifestations of a disease state are lessened and/or the time course of the progression is slowed or lengthened, as compared to a situation without treatment.

As used herein, "vector", "polynucleotide vector", "construct" and "polynucleotide construct" are used interchangeably herein. A polynucleotide vector of this invention may be in any of several forms, including, but not limited to, RNA, DNA, RNA encapsulated in a retroviral coat, DNA encapsulated in an adenovirus coat, DNA packaged in another viral or viral-like form (such as herpes simplex, and adeno-associated virus (AAV)), DNA encapsulated in liposomes, DNA complexed with polylysine, complexed with synthetic polycationic molecules, complexed with compounds such as polyethylene glycol (PEG) to immunologically "mask" the molecule and/or increase half-life, or conjugated to a non-viral protein. Preferably, the polynucleotide is DNA. As used herein, "DNA" includes not only bases A, T, C, and G, but also includes any of their analogs or modified forms of these bases, such as methylated nucleotides, internucleotide modifications such as uncharged linkages and thioates, use of sugar analogs, and modified and/or alternative backbone structures, such as polyamides.

Factor VIII Polypeptides

Novel DNA constructs and novel compositions comprising host cells producing polypeptides having FVIII activity are provided. The polypeptides having FVIII activity include deletion mutant proteins of FVIII in which a substantial part of the central region or "B domain" is deleted. Plasmid constructs comprised of DNA sequences encoding deletion polypeptides having FVIII activity are used to transform a host cell. The transformed host cell is then grown to express the gene. The host cell may be either an eukaryotic or a prokaryotic cell. Human FVIII has the sequence shown in FIGS. 1A and 1B (SEQ ID NO:1). The numbering of the amino acid sequence starts with A-1, the first amino acid after the 19 amino acid signal sequence. The last amino acid of FVIII is Y-2332. This numbering scheme is used throughout the specification.

The polypeptides of this invention include FVIII derivatives, namely compounds having at least one amino acid sequence with sequence similarity to the amino acid sequence of the natural form of human FVIII. The derivatives usually have a smaller number of amino acids than the natural form of human FVIII.

With the greater understanding of the structural requirements for FVIII cleavage and activation, we have designed a functional B domain deletion FVIII that is expressed and secreted as a single chain polypeptide so as to increase the recovery yield during pharmaceutical preparation. We tested the hypothesis that fusion of the N-terminal of the B domain with the amino acid sequences (from Glu-1649 to Pro-1688) of the A3-C1-C2 light chain would yield a single polypeptide FVIII molecule. As described in this invention, some FVIII derivatives possess typical thrombin activation profiles indistinguishable from wild-type FVIII and superior structural stability to wild-type FVIII as well as other B-domain deleted FVIII derivatives. Moreover, most of the derivatives have the added advantage of being expressed more efficiently in mammalian cells. This invention showed that a molecule devoid of most of domain B and part of domain A3, but still retains the maturation sites corresponding to amino acids 740 and 1689 (which appear to be necessary for the activation), exhibits normal procoagulant activity. This molecule can be activated by thrombin in the same manner as the natural human FVIII.

Novel polypeptides of interest will, for the most part, have a formula comprising an N-terminal heavy chain region, a linking spacer region, and a C-terminal light chain region. Schematic representation of B-domain deleted FVIII derivatives are presented in FIG. 2. The N-terminal heavy chain region is characterized as having an amino acid sequence corresponding to a consecutive sequence found in amino acid sequence A-1 through R-740 of the full-length human FVIII.

The linking spacer polypeptides consist of a short linking group of amino acid sequences corresponding substantially to domains B and A3-domain sequences (from S-741 to P-1688) with an internal deletion of amino acids 746 to 1649, 746 to 1652, 746 to 1655, 758 to 1649, 758 to 1652, 758 to 1655, 765 to 1649, 765 to 1652, 765 to 1655, 748 to 1658, 755 to 1658, 762 to 1658, 769 to 1658, 776 to 1658, or 783 to 1658.

The C-terminal light chain is characterized as having an amino acid sequence similar to a consecutive sequence of R-1689 through Y-2332 found in the sequence of FVIII. Variants of this invention, which embody internal deletions relative to the native FVIII molecule, preferably contain (i) an internal deletion described above; or (ii) deletions of fewer amino acids within the regions specified in (i). Other variants of this invention embodying internal deletions may contain deletions of one or more amino acids between R-1649 and P-1688 to fuse any amino acid sequence in A1, A2, and B domains. FIG. 2 shows the exemplary representation of dB747 and dBN(45-50) FVIII derivatives that have an internal deletion of amino acids 748 to 1658 and 746 to 1649 respectively, as compared to human FVIII.

These B-domain-deleted FVIII derivatives do not retain a site for intracellular proteolytic processing, such as residue Arg-1648, which results in the generation of homogenous FVIII derivatives comprising a major population of single chain polypeptides. The removal of the 80 kDa cleavage site (R-1648) did not decrease the activity of factor VIII generated in the conditioned media. In addition, some derivatives of this invention here showed no significant change in the thrombin activation fold. The present results here demonstrated that the removal of R-1648 did not affect the synthesis or secretion of the FVIII derivatives from the cell. In addition, the predominant FVIII species produced was a single chain molecule of approximately 170 kDa, the result of the loss of the intracellular processing site at the 80 kD site. The single-chain FVIII variants may be advantageous in that they may be produced in a more homogeneous form and may have an improved pharmacokinetic profile relative to natural human or other recombinant FVIII.

Figure 7:
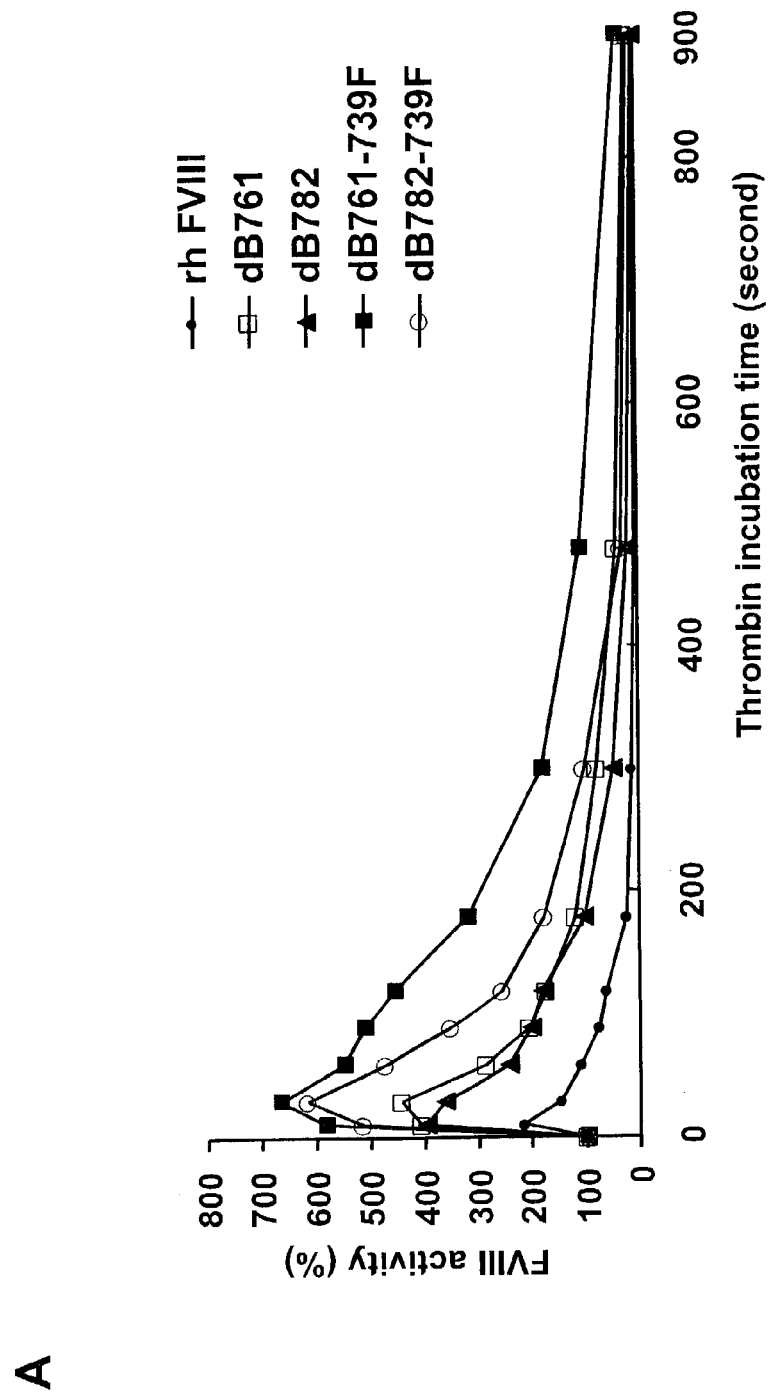
FIGS. 7A and 7B show comparison of thrombin activation kinetics of recombinant human FVIII and FVIII polypeptides.
Figure 7:
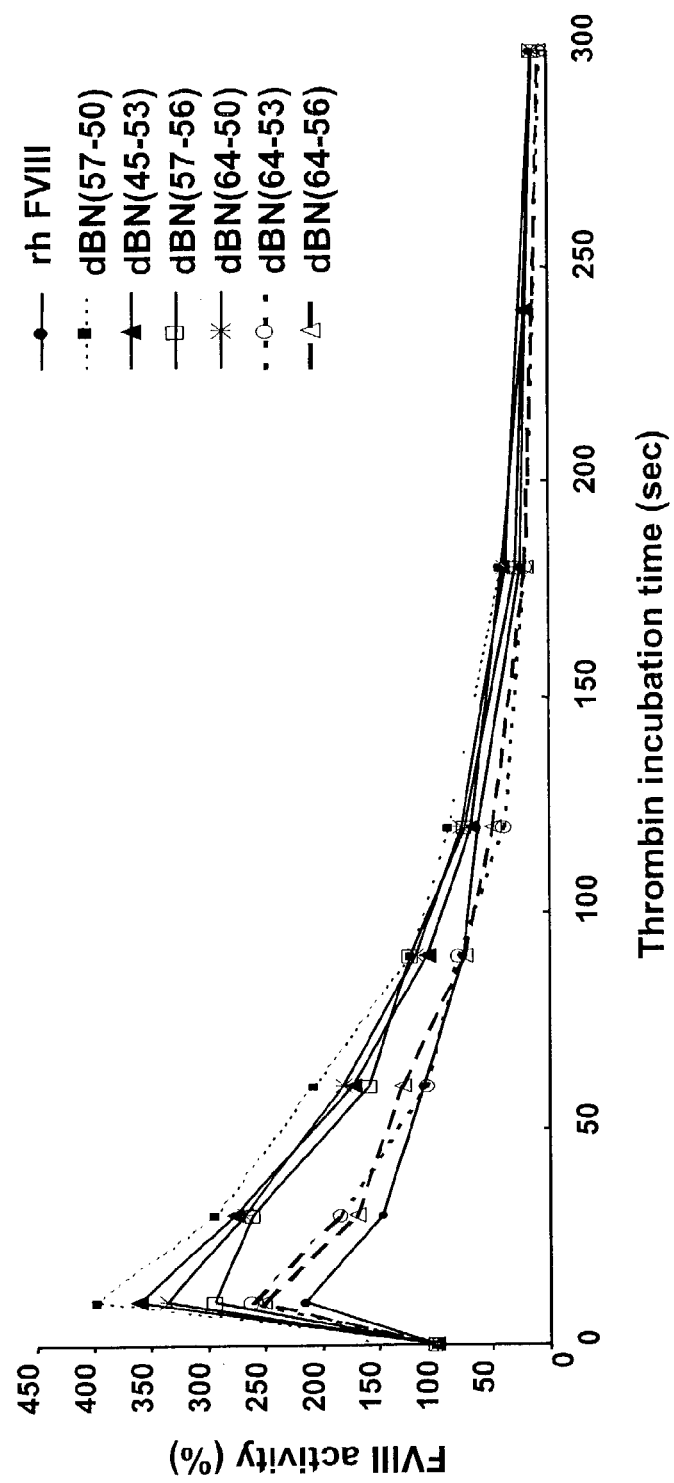

In full-length FVIII, thrombin cleavage after Arg residues 372, 740, and 1689 activates FVIII coagulant activity. This coincides with the generation of a FVIIIa heterotrimer consisting of the A1 subunit in a divalent-metal-ion-dependent association with the thrombin-cleaved A3-C1-C2 light chain and a free A2 subunit associated with the A1 domain through an ionic interaction. In full-length FVIII, cleavage after Arg-1689 removes an acidic amino acid rich region from R-1648 to R-1689, and is necessary for dissociation of FVIIIa from vWF and makes FVIIIa available for interaction with phospholipids. Analysis of the radiolabeled FVIII derivative proteins of this invention after thrombin digestion indicated a normal appearance of the 73 kD, and 50 and 40 kD fragments (See FIG. 5C). This result demonstrated that the disclosed FVIII derivatives can be activated by thrombin in the same manner as the complete natural molecule. As demonstrated in this invention, these FVIII derivatives exhibit typical thrombin activation that correlates with cleavage after Arg-372, Arg-740, and Arg-1689, generating an activated FVIII heterotrimer that is indistinguishable from wild-type FVIII and also is subject to rapid inactivation through dissociation of the A2 domain subunit (See FIG. 7).

One aspect of the invention relates to variants wherein an artificial N-linked glycosylation site is generated by fusing Asn amino acid in the B domain to an X-threonine or X-serine amino acid sequence in the A3 domain in concurrence with the deletion of the internal sequence as described above. Alternatively, a tripeptide sequence of the N-glycosylation recognition sequence (Asn-X-Ser/Thr where X can be any amino acid) in the fusion sites can be generated by linking the amino acids of 746, 758, and 765 located next to the Asn amino acid in the positions of 745, 757 and 764, respectively, directly to Ser or Thr amino acids in the positions of 1651, 1654, and 1657. These FVIII variants will have an internal deletion of amino acids 747 to 1650, 747 to 1653, 747 to 1656, 759 to 1650, 759 to 1653, 759 to 1656, 766 to 1650, 766 to 1653, or 766 to 1656, as compared to human FVIII. Consensus N-linked glycosylation sites contain tripeptide sequences of the formula asparagine-X-threonine or asparagine-X-serine, where X may be generally any amino acid. In particular, in one aspect of the invention, X may be any amino acid except proline. Variants of this aspect of the invention containing an engineered N-linked glycosylation site at the fusion sites between the B and A3 domains may prevent a potentially novel epitope sequence at the fusion site from being exposed to the immune system.

Another aspect of the invention relates to derivatives wherein one or more of the Factor Xa, APC and thrombin cleavage sites are modified to render such sites less labile to specific proteolysis. One subgenus of derivatives of particular interest at present includes those containing a modification at P-739 wherein the phenylalanine is preferred at present, but can be replaced by a different amino acid or deleted. Synthesis and secretion of the FVIII derivatives with modification of the amino acid at 739 in the invention was not affected. These variants exhibit higher activation rate by thrombin than full-length FVIII as well as other FVIII derivatives of this invention (see FIG. 7). The increased activity may be attributable to resistance to inactivation by Factor Xa cleavage in the chromogenic assay. Thus, this alteration appears to generate a more stable form of FVIII with the additional benefit of increased activity. However, it was found that, according to U. S. Pat. Nos. 5,422,260 and 5,451,521, a B-domain deleted FVIII derivative with the mutation of the arginine to an isoleucine at position 740 possessed less activity after the mutation.

Even though it may be assumed that all polypeptide FVIII molecules which are generated by fusion of the N-terminal region of the B domain with the amino acid sequences (from Glu-1649 to Pro-1688) of the A3-C1-C2 light chain would yield a similar profile of procoagulant activity, individual B-domain deleted FVIII derivatives were found to possess unique thrombin activation profile and structural stability in this invention. Therefore, we characterized in detail the molecular feature of individual B-domain deleted FVIII derivative in this invention to find an active safe single chain B-domain deleted FVIII derivative with similar profiles of thrombin activation and improved productivity.

Nucleic Acid Encoding Factor VIII Polypeptide

By "isolated" polynucleotide sequence, it is intended to encompass a nucleic acid molecule, DNA or RNA, which has been removed from its native environment. This includes segments of DNA encoding the FVIII polypeptide of the present invention, and may further comprise heterologous sequences such as vector sequences or other foreign DNA. For example, recombinant DNA molecules contained in a vector are considered isolated for the purposes of the present invention, which may be partially or substantially purified.

In addition, isolated nucleic acid molecules of the invention include DNA molecules, which comprise a sequence substantially different from those described above but which, either due to the degeneracy of the genetic code or other variability, still encode the FVIII polypeptide of the invention. Thus, it would be routine for one skilled in the art to generate the variants described above, for instance, to optimize codon expression or general function for a particular host.

In another aspect, the invention provides an isolated nucleic acid molecule comprising a polynucleotide which hybridizes under stringent hybridization conditions to a portion of a polynucleotide in a nucleic acid molecule of the invention described above. Hybridizing polynucleotides are useful as probes and primers as discussed above. Portions of a polynucleotide which hybridize to the FVIII polypeptide encoding sequence, which may be precisely specified by 5' and 3' base positions or by size in nucleotide bases as described above or precisely excluded in the same manner. Similarly, portions of a polynucleotide, which hybridize to the FVIII polypeptide, which may be used as probes and primers as well. Preferred hybridizing polynucleotides of the present invention are those that, when labeled and used in a hybridization assay known in the art (e.g. Southern and Northern blot analysis), display the greatest signal strength regardless of other heterologous sequences present in equimolar amounts.

In selecting a preferred host cell for transfection by the vectors of the invention, which comprise DNA sequences encoding both FVIII derivatives and for example, dihydrofolate reductase (DHFR) protein, it is appropriate to select the host according to the type of DHFR protein employed. If wild type DHFR protein is employed, it is preferable to select a host cell which is deficient in DHFR, thus permitting the use of the DHFR coding sequence as a marker for successful transfection in selective medium which lacks hypoxanthine, glycine, and thymidine.

On the other hand, if DHFR protein with low binding affinity for methotrexate (MTX) is used as the regulatory sequence, it is not necessary to use DHFR resistant cells. Mutant DHFR is resistant to MTX, therefore, MTX containing media can be used as a means of selection provided that the host cells themselves are MTX sensitive. Alternatively, a wild type DHFR gene may be employed as an amplification marker in a host cell which is not deficient in DHFR provided that a second drug selectable marker is employed, such as hygromycin resistance. Examples which are set forth describe the use of CHO cells (CHO-DBX11 cells) resistant to MTX as host cells and on vectors which employ the CMV and SV40 promoter as regulatory sequences to drive the on of FVIII derivatives and DHFR, respectively.

Variant and Mutant Polynucleotides

Such nucleic acid variants include those produced by nucleotide substitutions, deletions, or additions. The substitutions, deletions, or additions may involve one or more nucleotides. Alterations in the amino acid sequence may produce conservative or non-conservative amino acid substitutions, deletions or additions. Especially preferred among these are silent substitutions, additions and deletions, which do not alter the properties and activities of the polypeptides of the present invention or portions thereof. Also preferred in this regard are conservative substitutions.

The invention allows for the use of sequences in expression vectors, as well as to transfect host cells and cell lines, be these prokaryotic or eukaryotic cells. The invention also allows for purification of the polypeptides expressed from the expression vector. The expression vector may contain various molecular tags for easy purification. Subsequently obtained expression construct may be transformed into any host cell of choice. Cell lysates from the host cell is isolated by established methods well known in the field.

Variant and Mutant Polypeptides

To improve or alter the characteristics of FVIII polypeptide of the present invention, amino acid engineering may be employed. Recombinant DNA technology known to those skilled in the art can be used to create novel mutant polypeptides including single or multiple amino acid substitutions, deletions, additions, or fusion proteins. Such modified polypeptides can show, e.g., increased/decreased activity or increased/decreased stability. In addition, they may be purified in higher yields and show better solubility than the corresponding natural polypeptide, at least under certain purification and storage conditions.

Antibodies

In one embodiment, the present invention is directed to detecting presence of FVIII polypeptide using a variety of detection methods. One way to detect Factor VIII polypeptide is to label a ligand that specifically binds to the FVIII polypeptide. Such a ligand may be an antibody.

Purified FVIII polypeptide may be used to produce monoclonal or polyclonal antibody. Fragments of Factor VIII polypeptide also can be used to produce monoclonal or polyclonal antibody. Subsequently obtained monoclonal or polyclonal antibody can be used to determine the presence of FVIII polypeptide in various samples including cells, tissues, and body fluids such as but not limited to blood, serum, plasma, and urine. FVIII polypeptide may be assayed using a variety of molecular biological methods, which include but are not limited to in situ hybridization, immunoprecipitation, immunofluorescence staining, Western blot analysis and so on. One can carry out ELISA by using monoclonal antibody against FVIII polypeptide to determine the amount of FVIII polypeptide in the biological sample, including body fluids of human subjects believed to be suffering from a blood clotting disorder, such as hemophilia.

Antibodies of the invention include, but are not limited to, polyclonal, monoclonal, multispecific, human, humanized or chimeric antibodies, single chain antibodies, Fab fragments, F(ab') fragments, fragments produced by a Fab expression library, anti-idiotypic (anti-Id) antibodies (including, e.g., anti-Id antibodies to antibodies of the invention), and epitope-binding fragments of any of the above. The term "antibody," as used herein, refers to immunoglobulin molecules and immunologically active portions of immunoglobulin molecules, i.e., molecules that contain an antigen binding site that immunospecifically binds an antigen. The immunoglobulin molecules of the invention can be of any type (e.g., IgG, IgE, IgM, IgD, IgA and IgY), class (e.g., IgG1, IgG2, IgG3, IgG4, IgA1 and IgA2) or subclass of immunoglobulin molecule.

The antibodies of the present invention may be monospecific, bispecific, trispecific or of greater multispecificity. Multispecific antibodies may be specific for different epitopes of a polypeptide of the present invention or may be specific for both a polypeptide of the present invention as well as for a heterologous epitope, such as a heterologous polypeptide or solid support material.

Antibodies of the present invention may be described or specified in terms of the epitope(s) or portion(s) of a polypeptide of the present invention, which they recognize or specifically bind. The epitope(s) or polypeptide portion(s) may be specified as described herein, e.g., by the glycosylation site, N-terminal and C-terminal positions, or by size in contiguous amino acid residues.

Antibodies of the present invention may be used, for example, but not limited to, to purify, detect, and target the polypeptides of the present invention, including both in vitro and in vivo diagnostic and therapeutic methods. For example, the antibodies have use in immunoassays for qualitatively and quantitatively measuring levels of FVIII polypeptide of the present invention in biological samples.

As discussed in more detail below, the antibodies of the present invention may be used either alone or in combination with other compositions. The antibodies may further be recombinantly fused to a heterologous polypeptide at the N- or C-terminus or chemically conjugated (including covalent and non-covalent conjugations) to polypeptides or other compositions. For example, antibodies of the present invention may be recombinantly fused or conjugated to molecules useful as labels in detection assays and effector molecules such as heterologous polypeptides, drugs, radionuclides, or toxins.

The antibodies of the present invention may be generated by any suitable method known in the art. Polyclonal antibodies to an antigen of interest can be produced by various procedures well known in the art. For example, a polypeptide of the invention can be administered to various host animals including, but not limited to, rabbits, mice, rats, etc. to induce the production of sera containing polyclonal antibodies specific for the antigen. Various adjuvants may be used to increase the immunological response, depending on the host species, and include but are not limited to, Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and corynebacterium parvum. Such adjuvants are also well known in the art.

Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art. The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced.

Methods for producing and screening for specific antibodies using hybridorna technology are routine and well known in the art. In a non-limiting example, mice can be immunized with a Factor VIII polypeptide or a cell expressing such entity. Once an immune response is detected, e.g., antibodies specific for the antigen are detected in the mouse serum, the mouse spleen is harvested and splenocytes isolated. The splenocytes are then fused by well known techniques to any suitable myeloma cells, for example cells from cell line SP20 available from the ATCC. Hybridomas are selected and cloned by limited dilution. The hybridoma clones are then assayed by methods known in the art for cells that secrete antibodies capable of binding a polypeptide of the invention or its complex with its binding partner. Ascites fluid, which generally contains high levels of antibodies, can be generated by immunizing mice with positive hybridoma clones.

Antibodies may also be attached to solid supports, which are particularly useful for inimunoassays or purification of the target antigen. Such solid supports include, but are not limited to, glass, cellulose, polyacrylamide, nylon, polystyrene, polyvinyl chloride or polypropylene.

Assays For Antibody Binding

The antibodies of the invention may be assayed for immunospecific binding by any method known in the art. The immunoassays which can be used include but are not limited to competitive and non-competitive assay systems using techniques such as Western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, to name but a few. Such assays are routine and well known in the art (see, e.g., Ausubel et al, eds, 1994, Current Protocols in Molecular Biology, Vol. 1, John Wiley & Sons, Inc., New York, which is incorporated by reference herein in its entirety). Exemplary immunoassays are described briefly below but are not intended by way of limitation.

Immunoprecipitation protocols generally comprise lysing a population of cells in a lysis buffer such as RIPA buffer (1% NP-40 or Triton X-100, 1% sodium deoxycholate, 0.1% SDS, 0.15 M NaCl, 0.01 M sodium phosphate at pH 7.2, 1% Trasylol) supplemented with protein phosphatase and/or protease inhibitors (e.g., EDTA, PMSF, aprotinin, sodium vanadate), adding the antibody of interest to the cell lysate, incubating for a period of time (e.g., 1–4 hours) at 4° C., adding protein A and/or protein G sepharose beads to the cell lysate, incubating for about an hour or more at 4° C., washing the beads in lysis buffer and resuspending the beads in SDS/sample buffer. The ability of the antibody of interest to immunoprecipitate a particular antigen can be assessed by, e.g., Western blot analysis. One of skill in the art would be knowledgeable as to the parameters that can be modified to increase the binding of the antibody to an antigen and decrease the background (e.g., pre-clearing the cell lysate with sepharose beads). For further discussion regarding immunoprecipitation protocols see, e.g., Ausubel et al, eds, 1994, Current Protocols in Molecular Biology, Vol. 1, John Wiley & Sons, Inc., New York at 10.16.1.

Western blot analysis generally comprises preparing protein samples, electrophoresis of the protein samples in a polyacrylamide gel (e.g., 8%–20% SDS-PAGE depending on the molecular weight of the antigen), transferring the protein sample from the polyacrylamide gel to a membrane such as nitrocellulose, PVDF or nylon, blocking the membrane in blocking solution (e.g., PBS with 3% BSA or non-fat milk), washing the membrane in washing buffer (e.g., PBS-Tween 20), blocking the membrane with primary antibody (the antibody of interest) diluted in blocking buffer, washing the membrane in washing buffer, blocking the membrane with a secondary antibody (which recognizes the primary antibody, e.g., an anti-human antibody) conjugated to an enzymatic substrate (e.g., horseradish peroxidase or alkaline phosphatase) or radioactive molecule (e.g., $^{32}$P or $^{125}$I) diluted in blocking buffer, washing the membrane in wash buffer, and detecting the presence of the antigen. One of skill in the art would be knowledgeable as to the parameters that can be modified to increase the signal detected and to reduce the background noise. For further discussion regarding western blot protocols see, e.g., Ausubel et al, eds, 1994, Current Protocols in Molecular Biology, Vol. 1, John Wiley & Sons, Inc., New York at 10.8.1.

ELISAs comprise preparing antigen, which may include a sample comprising Factor VIII polypeptide, coating the well of a 96 well microtiter plate with the antigen, adding the antibody of interest conjugated to a detectable compound such as an enzymatic substrate (e.g., horseradish peroxidase or alkaline phosphatase) to the well and incubating for a period of time, and detecting the presence of the antigen. In ELISAs the antibody of interest does not have to be conjugated to a detectable compound; instead, a second antibody (which recognizes the antibody of interest) conjugated to a detectable compound may be added to the well. Further, instead of coating the well with the antigen, the antibody may be coated to the well. In this case, a second antibody conjugated to a detectable compound may be added simultaneously or following the addition of the antigen of interest to the coated well. One of skill in the art would be knowledgeable as to the parameters that can be modified to increase the signal detected as well as other variations of ELISAs known in the art. For further discussion regarding ELISAs see, e.g., Ausubel et al, eds, 1994, Current Protocols in Molecular Biology, Vol. 1, John Wiley & Sons, Inc., New York at 11.2.1.

Gene Therapy

In a specific embodiment, nucleic acids comprising sequences encoding the Factor VIII polypeptide are administered to treat, inhibit or prevent a disease or disorder associated with aberrant expression and/or activity of a polypeptide of the invention, by way of gene therapy. Gene therapy refers to therapy performed by the administration to a subject of an expressed or expressible nucleic acid. In this embodiment of the invention, the nucleic acids produce their encoded protein that mediates a therapeutic effect.

Any of the methods for gene therapy available in the art can be used according to the present invention. Exemplary methods are described below.

For general reviews of the methods of gene therapy, see Goldspiel et al., Clinical Pharmacy 12:488–505 (1993); Wu and Wu, Biotherapy 3:87–95 (1991); Tolstoshev, Ann. Rev. Pharmacol. Toxicol. 32:573–596 (1993); Mulligan, Science 260:926–932 (1993); and Morgan and Anderson, Ann. Rev. Biochem. 62:191–217 (1993); May, TIBTECH 11(5):155–215 (1993). Methods commonly known in the art of recombinant DNA technology which can be used are described in Ausubel et al. (eds.), Current Protocols in Molecular Biology, John Wiley & Sons, NY (1993); and Kriegler, Gene Transfer and Expression, A Laboratory Manual, Stockton Press, NY (1990).

In a preferred aspect, nucleic acid sequences may encode a Factor VIII polypeptide, in which the nucleic acid sequences are part of expression vectors that express the polypeptides in a suitable host. In particular, such nucleic acid sequences have promoters operably linked to the polypeptide coding region, said promoter being inducible or constitutive, and, optionally, tissue-specific. In another particular embodiment, nucleic acid molecules are used in which the polypeptide coding sequences and any other desired sequences are flanked by regions that promote homologous recombination at a desired site in the genome, thus providing for intrachromosomal expression of the antibody encoding-nucleic acids (Koller and Smithies, Proc. Natl. Acad. Sci. USA 86:8932–8935 (1989); Zijlstra et al., Nature 342:435–438 (1989).

Delivery of the nucleic acids into a patient may be either direct, in which case the patient is directly exposed to the nucleic acid or nucleic acid- carrying vectors, or indirect, in which case, cells are first transformed with the nucleic acids in vitro, then transplanted into the patient. These two approaches are known, respectively, as in vivo or ex vivo gene therapy.

In a specific embodiment, the nucleic acid sequences are directly administered in vivo, where it is expressed to produce the encoded product. This can be accomplished by any of numerous methods known in the art, e.g., by constructing them as part of an appropriate nucleic acid expression vector and administering them so that they become intracellular, e.g., by infection using defective or attenuated retrovirals or other viral vectors, or by direct injection of naked DNA, or coating with lipids or cell-surface receptors or transfecting agents, encapsulation in liposomes, microparticles, or microcapsules, or by administering them in linkage to a peptide which is known to enter the nucleus, by administering it in linkage to a ligand subject to receptor-mediated endocytosis (see, e.g., Wu and Wu, J. Biol. Chem. 262:4429–4432 (1987)) (which can be used to target cell types specifically expressing the receptors) and so on. In another embodiment, nucleic acid-ligand complexes can be formed in which the ligand comprises a fusogenic viral peptide to disrupt endosomes, allowing the nucleic acid to avoid lysosomal degradation. In yet another embodiment, the nucleic acid can be targeted iii vivo for cell specific uptake and expression, by targeting a specific receptor. Alternatively, the nucleic acid can be introduced intracellularly and incorporated within host cell DNA for expression, by homologous recombination (Koller and Smithies, Proc. Natl. Acad. Sci. USA 86:8932–8935 (1989); Zijlstra et al., Nature 342:435–438 (1989)).

In a specific embodiment, viral vectors that contain nucleic acid sequences encoding the polypeptide are used. The nucleic acid sequences encoding the polypeptide to be used in gene therapy are cloned into one or more vectors, which facilitates delivery of the gene into a patient. Retroviral vectors, adenoviral vectors and adeno-associated viruses are examples of viral vectors that may be used. Retroviral vectors contain the components necessary for the correct packaging of the viral genome and integration into the host cell DNA.

Another approach to gene therapy involves transferring a gene to cells in tissue culture by such methods as electroporation, lipofection, calcium phosphate mediated transfection, or viral infection. Usually, the method of transfer includes the transfer of a selectable marker to the cells. The cells are then placed under selection to isolate those cells that have taken up and are expressing the transferred gene. Those cells are then delivered to a patient.

In this embodiment, the nucleic acid is introduced into a cell prior to administration in vivo of the resulting recombinant cell. Such introduction can be carried out by any method known in the art, including but not limited to transfection, electroporation, microinjection, infection with a viral or bacteriophage vector containing the nucleic acid sequences, cell fusion, chromosome-mediated gene transfer, microcell-mediated gene transfer, spheroplast fusion and so on. Numerous techniques are known in the art for the introduction of foreign genes into cells and may be used in accordance with the present invention, provided that the necessary developmental and physiological functions of the recipient cells are not disrupted. The technique should provide for the stable transfer of the nucleic acid to the cell, so that the nucleic acid is expressible by the cell and preferably heritable and expressible by its cell progeny.

Cells into which a nucleic acid can be introduced for purposes of gene therapy encompass any desired, available cell type, and include but are not limited to epithelial cells, endothelial cells, keratinocytes, fibroblasts, muscle cells, hepatocytes; blood cells such as T-lymphocytes, B-lymphocytes, monocytes, macrophages, neutrophils, eosinophils, megakaryocytes, granulocytes; various stem or progenitor cells, in particular hematopoietic stem or progenitor cells, e.g., as obtained from bone marrow, umbilical cord blood, peripheral blood, fetal liver, and so on.

In a preferred embodiment, the cell used for gene therapy is autologous to the patienft.

In an embodiment in which recombinant cells are used in gene therapy, nucleic acid sequences encoding the polypeptide are introduced into the cells such that they are expressible by the cells or their progeny, and the recombinant cells are then administered in vivo for therapeutic effect. In a specific embodiment, stem or progenitor cells are used. Any stem and/or progenitor cells which can be isolated and maintained in vitro can potentially be used in accordance with this embodiment of the present invention.

In a specific embodiment, the nucleic acid to be introduced for purposes of gene therapy comprises an inducible promoter operably linked to the coding region, such that expression of the nucleic acid is controllable by controlling the presence or absence of the appropriate inducer of transcription.

Therapeutic Composition

In one embodiment, the present invention relates to treatment for blood clotting diseases. In this way, the inventive therapeutic compound may be administered to human patients who are either suffering from, or prone to suffer from the disease by providing compounds that stimulate blood coagulation. In particular, the disease may be hemophilia, in particular, hemophilia A.

The formulation of therapeutic compounds is generally known in the art and reference can conveniently be made to Remington's Pharmaceutical Sciences, 17th ed., Mack Publishing Co., Easton, Pa., USA. For example, from about 0.05 µg to about 20 mg per kilogram of body weight per day may be administered. Dosage regime may be adjusted to provide the optimum therapeutic response. For example, several divided doses may be administered daily or the dose may be proportionally reduced as indicated by the exigencies of the therapeutic situation. The active compound may be administered in a convenient manner such as by the oral, intravenous (where water soluble), intramuscular, subcutaneous, intra nasal, intradermal or suppository routes or implanting (eg using slow release molecules by the intraperitoneal route or by using cells e.g. monocytes or dendritic cells sensitised in vitro and adoptively transferred to the recipient). Depending on the route of administration, the peptide may be required to be coated in a material to protect it from the action of enzymes, acids and other natural conditions which may inactivate said ingredients.

For example, the low lipophilicity of the peptides will allow them to be destroyed in the gastrointestinal tract by enzymes capable of cleaving peptide bonds and in the stomach by acid hydrolysis. In order to administer peptides by other than parenteral administration, they will be coated by, or administered with, a material to prevent its inactivation. For example, peptides may be administered in an adjuvant, co-administered with enzyme inhibitors or in liposomes. Adjuvants contemplated herein include resorcinols, non-ionic surfactants such as polyoxyethylene oleyl ether and n-hexadecyl polyethylene ether. Enzyme inhibitors include pancreatic trypsin inhibitor, diisopropylfluorophosphate (DEP) and trasylol. Liposomes include water-in-oil-in-water CGF emulsions as well as conventional liposomes.

The active compounds may also be administered parenterally or intraperitoneally. Dispersions can also be prepared in glycerol liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions (where water soluble) or dispersions and sterile powders for the extemporaneous preparation of sterile injectable solutions or dispersion. In all cases the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of superfactants. The prevention of the action of microorganisms can be brought about by various antibacterial and antifungal agents, for example, chlorobutanol, phenol, sorbic acid, theomersal and the like. In many cases, it will be preferable to include isotonic agents, for example, sugars or sodium chloride. Prolonged absorption of the injectable compositions can be brought about by the use in the composition of agents delaying absorption, for example, aluminium monostearate and gelatin.

Sterile injectable solutions are prepared by incorporating the active compounds in the required amount in the appropriate solvent with various other ingredients enumerated above, as required, followed by filtered sterilization. Generally, dispersions are prepared by incorporating the various sterile active ingredient into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from a previously sterile-filtered solution thereof.

When the peptides are suitably protected as described above, the active compound may be orally administered, for example, with an inert diluent or with an assimilable edible carrier, or it may be enclosed in hard or soft shell gelatin capsule, or it may be compressed into tablets, or it may be incorporated directly with the food of the diet. For oral therapeutic administration, the active compound may be incorporated with excipients and used in the form of ingestible tablets, buccal tablets, troches, capsules, elixirs, suspensions, syrups, wafers, and the like. Such compositions and preparations should contain at least 1% by weight of active compound. The percentage of the compositions and preparations may, of course, be varied and may conveniently be between about 5 to about 80% of the weight of the unit. The amount of active compound in such therapeutically useful compositions is such that a suitable dosage will be obtained. Preferred compositions or preparations according to the present invention are prepared so that an oral dosage unit form contains between about 0.1 µg and 2000 mg of active compound.

The tablets, pills, capsules and the like may also contain the following: A binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed. In addition, the active compound may be incorporated into sustained-release preparations and formulations.

As used herein "pharmaceutically acceptable carrier and/or diluent" includes any and all solvents, dispersion media, coatings antibacterial and antifungal agents, isotonic and absorption delaying agents and the like. The use of such media and agents for pharmaceutical active substances is well known in the art. Except insofar as any conventional media or agent is incompatible with the active ingredient, use thereof in the therapeutic compositions is contemplated. Supplementary active ingredients can also be incorporated into the compositions.

It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active material calculated to produce the desired therapeutic effect in association with the required pharmaceutical carrier. The specification for the dosage unit forms of the invention are dictated by and directly dependent on (a) the unique characteristics of the active material and the particular therapeutic effect to be achieved, and (b) the limitations inherent in the art of compounding such an active material for the treatment of disease in living subjects having a diseased condition in which bodily health is impaired.

The principal active ingredient is compounded for convenient and effective administration in effective amounts with a suitable pharmaceutically acceptable carrier in dosage unit form. A unit dosage form can, for example, contain the principal active compound in amounts ranging from 0.5 µg to about 2000 mg. Expressed in proportions, the active compound is generally present in from about 0.5 µg/ml of carrier. In the case of compositions containing supplementary active ingredients, the dosages are determined by reference to the usual dose and manner of administration of the said ingredients.

Delivery Systems

Various delivery systems are known and can be used to administer a compound of the invention, e.g., encapsulation in liposomes, microparticles, microcapsules, recombinant cells capable of expressing the compound, receptor-mediated endocytosis, construction of a nucleic acid as part of a retroviral or other vector, etc. Methods of introduction include but are not limited to intradermal, intramuscular, intraperitoneal, intravenous, subcutaneous, intranasal, epidural, and oral routes. The compounds or compositions may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the pharnaccutical compounds or compositions of the invention into the central nervous system by any suitable route, including intraventricular and intrathecal injection; intraventricular injection may be facilitated by an intraventricular catheter, for example, attached to a reservoir, such as an Ominaya reservoir. Pulmonary administration can also be employed, e.g., by use of an inhaler or nebulizer, and formulation with an aerosolizing agent.

In a specific embodiment, it may be desirable to administer the pharmaceutical compounds or compositions of the invention locally to the area in need of treatment; this may be achieved by, for example, and not by way of limitation, local infusion during surgery, topical application, e.g., in conjunction with a wound dressing after surgery, by injection, by means of a catheter, by means of a suppository, or by means of an implant, said implant being of a porous, nonporous, or gelatinous material, including membranes, such as sialastic membranes, or fibers. Preferably, when administering a protein, including an antibody or a peptide of the invention, care must be taken to use materials to which the protein does not absorb. In another embodiment, the compound or composition can be delivered in a vesicle, in particular a liposome. In yet another embodiment, the compound or composition can be delivered in a controlled release system. In one embodiment, a pump may be used. In another embodiment, polymeric materials can be used. In yet another embodiment, a controlled release system can be placed in proximity of the therapeutic target, i.e., the brain, thus requiring only a fraction of the systemic dose.

A composition is said to be "phannacologically or physiologically acceptable" if its administration can be tolerated by a recipient animal and is otherwise suitable for administration to that animal. Such an agent is said to be administered in a "therapeutically effective amount" if the amount administered is physiologically significant. An agent is physiologically significant if its presence results in a detectable change in the physiology of a recipient patient.

Mammalian cell culture is the preferred method of expressing exogenous DNA to produce the functional human FVIII derivatives disclosed in this invention. In particular, common mammalinan cells used for production of recombinant proteins, such as Chinese hamster ovary (CHO) cell lines, Baby hamster kidney (BHK) cell line, COS cell lines, and Madin Darby canine kidney (MDCK) cell line are of interest. Expression vectors for such cells ordinarily include (if necessary) (an) origin(s) of replication, a promoter located in front of the gene to be expressed, along with any necessary ribosome binding sites, RNA splice sites, polyadenylation site, and transcriptional terminator sequences.

For use in mammalian cells, the regulatory functions on the expression vectors may be provided by viral material. For example, commonly used promoters are derived from elongation factor-1 (EF-1), Simian Virus 40 (SV40) and most particularly Cytomegalovirus (CMV). Furthermore, it is also possible, and often desirable, to utilize promoter or regulatory sequences normally associated with the desired gene sequence, provided such regulatory sequences are compatible with the host cell systems.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims. The following examples are offered by way of illustration of the present invention, and not by way of limitation.

EXAMPLES

Example 1

Cloning of Full-length FVIII cDNA

Reverse transcription was performed using gene specific primer (F8B10, 5'AGCACAAAGGTAGAAGGCAAGC3' (SEQ ID NO:2)) which covers nucleotides 7237–7258 of published sequence (GenBank accession number: NM 00132). Briefly, 50 ug of human liver mRNA, 1 ul of 10× reverse transcription buffer, 1 μM of F8B10 primer, 4 mM dNTPs, 1 unit of RNAse inhibitor, and 10 units of reverse transcriptase were added in a 9.5 ul total volume reaction mixture. The reaction was then incubated for 90 min at 42° C. Synthesized cDNA was amplified by a standard PCR protocol using pfu polymerase and the three sets of gene-specific primers. The first primer set covers nucleotides 133–1997 of published sequence (GenBank accession number: NM 00132): F8FD (FW, 5'C.CTTTTGCTTCTCCAGT-TGAAC3' (SEQ ID NO:3)) and F8BD (BW, 5'TTCTCTGT-GAGGTACCAGCTTC3' (SEQ ID NO:4)). The second and third set of primers cover nucleotides 1810–4295 and 4044–7320 respectively: F8FC (FW 5'TGCCTGACCCGC-TATTACTCTA3' (SEQ ID NO:5)) and F8BB (BW, 5' TCTATCTGTGTGAGGGTGCTCG3' (SEQ ID NO:6)); F8FA (FW 5'GGAGGAAGAAAACTTGGAAGGC3' (SEQ ID NO:7)) and F8B10(see FIG. 3). PCR was performed using the following conditions: 1 cycle of denaturation at 95°C. for 1' 30", 45 cycles of amplification (at 95° C. for 30 sec, at 56° C. for 30 sec and at 68° C. for 6 min) and 1 cycle extension at 68° C. for 10 min.

Figure 3:
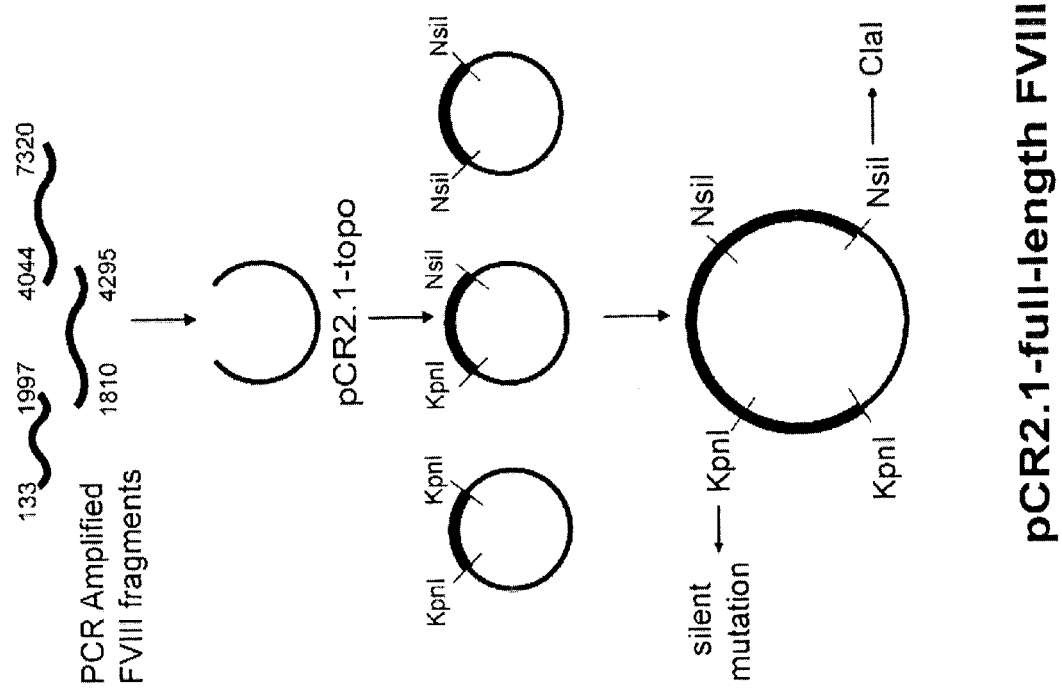
FIG. 3 shows a cDNA construction scheme for full-length FVIII.

As depicted schematically in FIG. 3, amplified fragments were subcloned into pCR2.1 TOPO vector. Three subcloned fragments were then joined into pCR2.1 TOPO vector using KpnI and NsiI as unique restriction sites. After joining the three fragments, the internal KpnI site in the FVIII coding region was removed by silent mutation, and the NsiI site in the pCR2.1 TOPO multicloning site was substituted with ClaI in order to remove the linked full-length FVIII cDNA with KpnI and ClaI digestion. Two restriction enzyme sites, XbaI and NotI, were removed from the pCR2.1 vector backbone for further cloning purposes. This modified vector was named pCR2. 1-full-length FVIII.

Example 2

Construction of Plasmids Carrying cDNA of the FVIII Derivatives which have Undergone Deletions in the Regions Corresponding to the B and A3 Domains Example 2A Construction of Plasmids for B-domain Deleted FVIII Derivatives with a Spacer of Various Size Linking the Carboxy-terminus of the Heavy Chain to the Amino Terminus of the Light Chain The starting plasmid, pCR2.1-fullFVIII, contains cDNA of full-length Factor VIII, nucleotides 133 to 7320. pCR2.1-fullFVIII was digested with EcoNI to delete nucleotides 2783 to 4804 from the full length FVIII. Cohesive ends of EcoNI-digested vector were blunted by DNA polymerase I Klenow fragment for ligation. This ligated vector was named pCR2.1-deltaEcoNI_FVIII and used as a template for furthermore, precise, deletion mutagenesis.

Oligonucleotide primers were designed to make a series of precise in-frame deletions. Each primer matches the sequences flanking both sides of the segments to be deleted. Delta-747, delta-754, delta-761, delta-768, delta-775 and delta-782 primers generate the fusion sites of Arg747-Gln1659, Lys754-Gln1659, Ile761-Gln1659, Lys768-Gln1659, His775-Gln1659 and Ile782-Gln1659, which respectively are:

(delta-747:
5'-CTTCTCCCAGAATTCAAGACAAGAGGAAATT (SEQ ID NO: 8))

GACTATG-3';

(delta-754:

```
                                              -continued
5'-CCTAGCACTAGGCAAAAGCAAGAGGAAATTG (SEQ ID NO: 9))

ACTATG-3';

(delta-761:
5'-CAATTTAATGCCACCACAATTCAAGAGGAAA (SEQ ID NO:10))

TTGACTATG-3';

(delta-768:
5'-CAGAAAATGACATAGAGAAGCAAGAGGAAAT (SEQ ID NO: 11))

TGACTATG-3';

(delta-775:
5'-GACCCTTGGTTTGCACACCAAGAGGAAATTG (SEQ ID NO: 12))

ACTATG-3';

(delta-782:
5'GCACACAGAACACCTATGCCTAAAATACAAGA (SEQ ID NO: 13))

GGAAATTGACTATGATGATACC-3'.
```

In addition to the mutagenic primers described above, a selection primer (5'-CGTGATCCATGTCGACGCCTGCT-TGCC-3' (SEQ ID NO:14)) which changes the original unique NcoI site into SalI was used for site-directed mutagenesis with the plasmid pCR2.1-deltaEcoNI_FVIII as a template. Restriction digestion was carried out to select positive clones, which were further verified by sequencing. Finally verified clones were named dB747, dB754, dB761, dB768, dB775, and dB782, respectively.

Example 2B

Generation of Plasmids Containing a new N-glycan Sequence in the Fusion Sites

To prevent exposure of a new epitope of unnatural amino acid sequence in the junction region of the heavy chain and the light chain, we created an N-glycosylation recognition sequence (Asn-X-Ser/Thr in which X can be any amino acid) in the fusion sites by linking Asn in the positions of 745, 757 and 764 of the B-domain to amino acids in the positions of 1650, 1653 and 1656 located next to Ser or Thr amino acids in the positions of 1651, 1654, and 1657, which generate a N-linked glycosylation site in the fusion sites. Oligonucleotide primers were designed to make a series of precise in-frame deletions. pCR2.1-deltaEcoNI_FVIII was used as a template for further precise deletion mutagenesis. Each primer matches the sequences flanking both sides of the segments to be deleted. N-745-1650, N-745-1653, N-745-1656, N-757-1650, N-757-1653, N-757-1656, N-764-1650, N-764-1653, and N-764-1656 primers generate the fusion sites of Asn745-Ile1650, Asn745-Thr1653, Asn745-Gln1656, Asn757-Ile1650, Asn757-Thr1653, Asn757-Gln1656, Asn764-Ile1650, Asn764-Thr1653, and Asn764-Gln1656. The nucleotide sequences of the oligonucleotide primers are as follows:

```
(N-745-1650:
5'-CAAGAAGCTTCTCCCAGAAAATAACTCGTAC (SEQ ID NO: 15))

TACTCTTC-3';

(N-745-1653:
5'-CAAGAAGCTTCTCCCAGAAAACTACTCTTCA (SEQ ID NO: 16))
```

-continued

```
GTCAGTC-3';

(N-745-1656:
5'-CAAGAAGCTTCTCCCAGAAACAGTCAGATCA (SEQ ID NO: 17))

AGAGGAAATTG-3';

(N-757-1650:
5'-CTAGGCAAAAGCAATTTAATATAACTCGTAC (SEQ ID NO: 18))

TACTCTTC-3';

(N-757-1563:
5'-CTAGGCAAAAGCAATTTAATACTACTCTTCA (SEQ ID NO: 19))

GTCAGTC-3';

(N-757-1656:
5'-CTAGGCAAAAGCAATTTAATCAGTCAGATCA (SEQ ID NO: 20))

AGAGGAAATTG-3';

(N-764-1650:
5'-CACCACAATTCCAGAAAATATAACTCGTACT (SEQ ID NO: 21))

ACTCTTC-3';

(N-764-1653:
5'-CACCACAATTCCAGAAAATACTACTCTTCAG (SEQ ID NO: 22))

TCAGTC-3';

(N-764-1656:
5'-CACCACAATTCCAGAAAATCAGTCAGATCAA (SEQ ID NO: 23))

GAGGAAATTG-3'.
```

In addition to those mutagenic primers described above, a selection primer (5'-CGTGATCCATGTCGACGCCTGCTTGCC-3' (SEQ ID NO:24)), which changes the original unique NcoI site into SalI was used for site-directed mutagenesis using the plasmid pCR2.1-deltaEcoNI_FVIII as a template. Restriction digestion was carried out to select positive clones, which were further verified by sequencing. Finally verified clones were named as dBN(45-50), dBN (45-53), dBN(45-56), dBN(57-50), dBN(57-53), dBN(57-56), dBN(64-50), dBN(64-56), respectively.

Example 3

Expression of the FVIII derivatives in Mammalian Cells

Example 3A

Construction of Mammalian Expression Vectors

From dB747, dB754, dB761, dB768, dB775, dB782, dB761-739F, dB783-739F, dBN(45-50), dBN(45-53), dBN (45-56), dBN(57-50), dBN(57-53), dBN(57-56), dBN(64-50), dBN(64-53), and dBN(64-56) plasmids, the cDNA sequence of Factor VIII derivatives were excised, blunt-ended, and cloned between the promoter of cytomegalovirus (CMV) and bovine growth hormone polyadenylation sequences (bGHpA). In all constructs, orientation of inserts was verified by restriction enzyme digestion and sequencing.

Example 3B

Transient Transfection of Mammalian Expression Constructs in BHK21 Cells

BHK21 cells were obtained from American Type Culture Collection (ATCC) and were maintained in EMEM supplemented with 10% fetal bovine serum. The day before transfection, cells were plated onto six-well tissue culture dishes at a density such that the cells reached 70–80% confluence by the time of transfection. Transfections utilized a liposome-based reagent. Each transfection was performed using 1 µg of FVIII derivative expression construct DNA and 30 ng of an internal control plasmid pSV β-galactosidase (Promega, Madison, Wis., USA). Four hours after transfection, the transfection medium was removed by aspiration, 2 ml of complete medium was added, and the plates were returned to the incubator. At 24 h post-transfection, medium was removed, spun down, and frozen at −80° C. Cell lysates were prepared and ,-galactosidase activities in cell lysates were measured using the Galacto-Light Plus Kit (Tropix, Mass., USA) following the manufacturer's instructions. The β-galactosidase activity, expressed from an internal control plasmid pSV β-galactosidase, provided an internal control to monitor transfection efficiency. FVIII activities were normalized based on the β-galactosidase activity in each well. An ELISA assay was used to determine the level of FVIII antigen present in medium samples (in triplicate). The procoagulant activity of the Factor VIII (FVIII:C) was quantified in culture medium (in triplicate) by using the FVIII Coatest chromogenic assay (Chromogenix, Molndal, Sweden).

The results are presented in Tables 1 and 2.

TABLE 1

Determination of the level of FVIII agtigen (FVIII: Ag) and of the FVIII procoagulant activity (FVIII: C) in the supernatant of BHK21 cultures transfected with the FVIII derivative expression vector at 24 h post transfection (results expressed in mU/ml or %/ml)

| Derivative | FVIII: Ag (mU/ml) | FVIII: C (%/ml) | Specific activity[a] |
|---|---|---|---|
| dB-747 | 77.8 ± 5.92 | 7.1 ± 0.61 | 0.09 |
| dB-754 | 89.9 ± 5.16 | 8.8 ± 0.28 | 0.10 |
| dB-761 | 72.8 ± 10.27 | 8.3 ± 0.54 | 0.11 |
| dB-768 | 85.6 ± 1.17 | 9.2 ± 0.44 | 0.11 |
| dB-775 | 75.5 ± 7.93 | 7.5 ± 0.32 | 0.10 |
| dB-782 | 76.3 ± 4.66 | 7.7 ± 0.46 | 0.10 |
| full-length FVIII | 5.2 ± 0.72 | 0.2 ± 0.01 | 0.04 |

[a]Calculated by dividing FVIII: C values with FVIII: Ag values

TABLE 2

Determination of the level of FVIII agtigen (FVIII: Ag) and of the FVIII procoagulant activity (FVIII: C) in the supernatant of BHK21 cultures transfected with the FVIII derivative expression vector at 24 h post transfection (results expressed in mU/ml or %/ml)

| Derivative | FVIII: Ag (mU/ml) | FVIII: C (%/ml) |
|---|---|---|
| dBN(45–50) | 81.4 ± 5.72 | 7.2 ± 0.73 |
| dBN(45–53) | 98.9 ± 2.57 | 8.4 ± 0.23 |
| dBN(45–56) | 88.6 ± 6.37 | 7.2 ± 0.75 |
| dBN(57–50) | 87.9 ± 11.1 | 8.1 ± 0.37 |
| dBN(57–53) | 82.4 ± 3.24 | 7.3 ± 0.54 |
| dBN(57–56) | 86.5 ± 8.15 | 7.6 ± 0.69 |
| dBN(64–50) | 87.4 ± 7.38 | 8.2 ± 0.53 |
| dBN(64–53) | 80.7 ± 5.56 | 7.5 ± 0.64 |
| dBN(64–56) | 84.9 ± 3.42 | 7.9 ± 0.41 |
| full-length FVIII | 5.5 ± 0.53 | 0.3 ± 0.06 |

The results show that the FVIII derivatives which have undergone deletion are biologically active in blood coagulation test, and that higher levels of protein is obtained with the FVIII derivative constructs than with the full-length FVIII. In addition, the ratio of FVIII:C to FVIII:Ag for the derivatives of this invention is higher than that of full-length FVIII, indicating that FVIII derivatives may be more stable after secretion into culture media. As shown in Table 3, the increases in FVIII activity (FVIII: C) of recombinant FVIII derivatives over time after incubation were higher as compared with that of recombinant full-length FVIII.

Example 4

Substitution of Pro with Phe at Position 739

Pro739 in the FVIII B-domain deleted variants described above were modified using the site-directed mutagenesis method. An oligonucleotide primer (5'-AACAATGCCAT-TGAATTCAGAAGCTTCTCCCAG-3' (SEQ ID NO:25)) was designed to introduce substitution of Pro with Phe at position 739. Whole mutagenesis procedures were identical with Example 2 described above. The vectors possessing Pro739Phe substitution in each B-domain deletion FVIII derivative were named as dB747-739F, dB754-739F, dB761-739F, dB768-739F, dB775-739F, dB782-739F, dBN(45-50)-739F, dBN(45-53)-739F, dBN(45-56)-739F, dBN(57-50)-739F, dBN(57-53)-739F, dBN(57-56)-739F, dBN(64-50)-739F, dBN(64-53)-739F, and dBN(64-56)-739F, respectively. The resultant DNAs were cloned into the mammalian expression vector, prepared, transfected, and resultant samples assayed as above. As showin in Table 4, dB761-739F and dB782-739F were found to generate more activity than dB761 and dB782, respectively, increased activity after the mutation of the proline to a phenylalanine at position 739.

TABLE 3

Determination of the FVIII procoagulant activity (FVIII: C) in the supernatant of BHK21 cultures transfected with the FVIII derivative expression vector at 24 h and 48 h post transfection (results expressed in %/ml)

| Derivative | 24 h | 48 h |
|---|---|---|
| dB-747 | 7.8 ± 0.09 | 15.9 ± 0.85 |
| dB-754 | 9.0 ± 0.28 | 17.9 ± 0.43 |
| dB-761 | 8.0 ± 0.22 | 16.0 ± 0.69 |
| dB-768 | 7.7 ± 0.31 | 18.0 ± 0.19 |
| dB-775 | 7.3 ± 0.44 | 14.9 ± 0.34 |
| dB-782 | 6.2 ± 0.12 | 14.2 ± 0.91 |
| full-length FVIII | 0.3 ± 0.09 | 0.2 ± 0.06 |

TABLE 4

Determination of the FVIII procoagulant activity (FVIII: C) in the supernatant of HEK293 cells stably transfected with the FVIII derivative expression vector (results expressed in %/ml/24 hrs)

| Derivative | One-stage assay | Two-stage assay | Ratio of two stage/ one stage activity |
|---|---|---|---|
| dB761 | 53.2 ± 2.90 | 85.4 ± 7.85 | 1.61 |
| dB761-739F | 79.5 ± 4.12 | 251.6 ± 14.57 | 3.16 |
| dB782 | 65.0 ± 3.47 | 70.1 ± 5.79 | 1.08 |
| dB782-739F | 62.6 ± 5.14 | 98.7 ± 9.15 | 1.58 |
| full-length FVIII | 10.2 ± 1.29 | 11.3 ± 1.34 | 1.11 |

Example 5

Establishment of HEK293 Cell Lines Expressing FVIII Derivatives

Example 5A

Construction of Plasmids used to Generate Mammalian Cells that Stably Express FVIII Derivatives.

Figure 4:
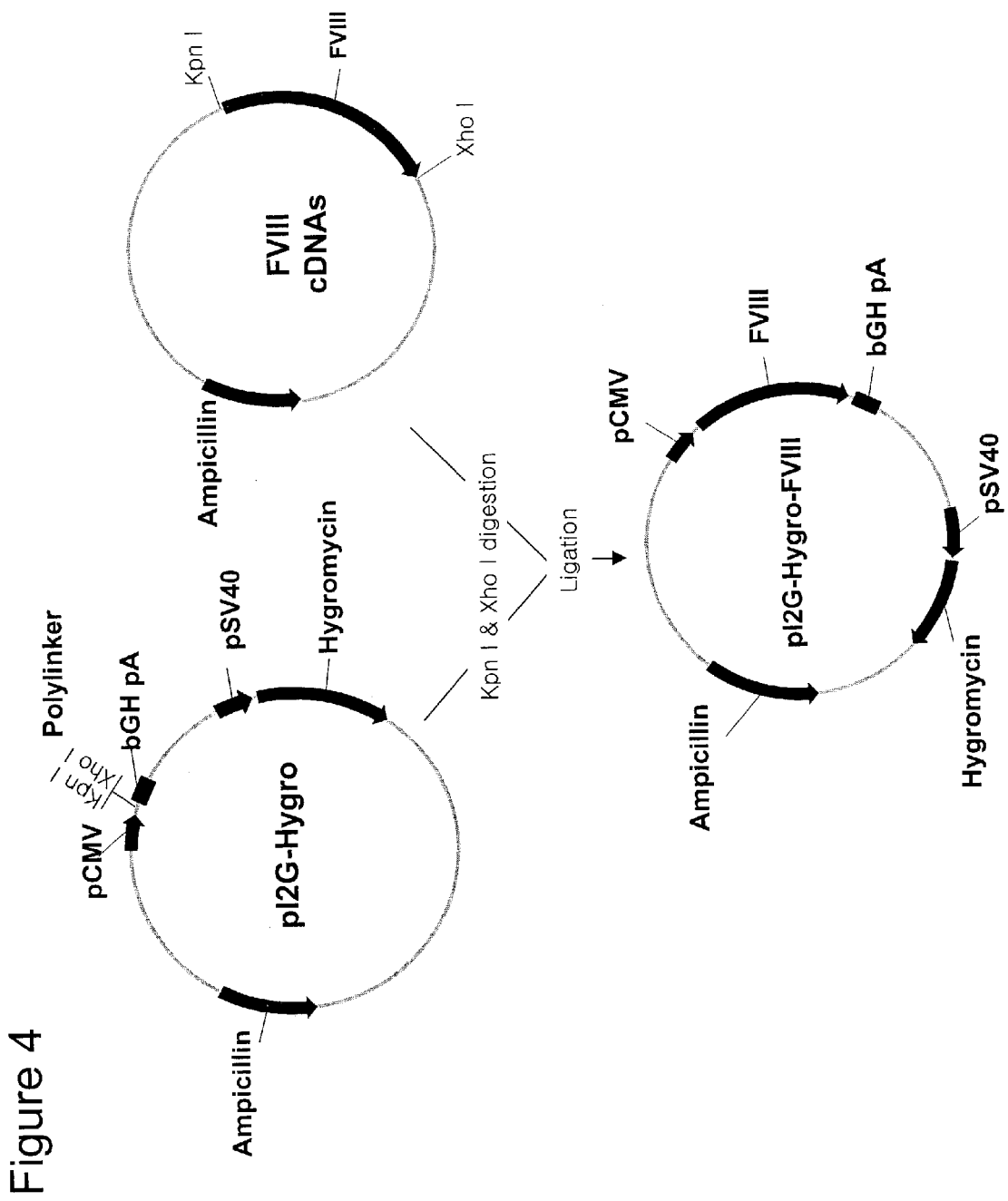
FIG. 4 shows a DNA construction scheme for FVIII derivatives in mammalian vector.

As shown in FIG. 4, the mammalian expression plasmid used in this Example was pI2G-Hygro which contains, in clockwise order, the cytomegalovirus promoter, polylinker, and bovine growth hormone polyadenylation signal sequence followed by a hygromycin resistance expression cassette driven by the SV40 promoter, and a gene coding ampicillin resistance. The polylinker of plasmid pI2G-Hygro was opened using Kpn1 and XhoI. Into this vector were ligated approximately 4.5 kb of Kpn1 and XhoI fragments containing the coding sequences for FVIII derivatives which were excised from the plasmids described in Examples 2, 3, and 4. Each pI2G-Hygro vector which has the coding sequence for individual Factor VIII derivative is referred to as pI2G-Hygro-"plasmid name for each FVIII derivative cDNA" (See Examples 2, 3, and 4). For example, the mammalian expression vector containing the coding sequences for dB747 and dBN(45-50) (in Examples 2 and 3) are referred to as pI2G-Hygro-dB47 and pI2G-Hygro- dBN (45-50), respectively.

Example 5B

Stable Transfection of 1EK293 Cells

The pI2G-hygro plasmids containing the transcription unit for each FVIII were linearized with MfeI and precipitated with phenol-chloroform and ethanol in preparation for HEK293 cell transfection. HEK293 cells were transfected via a liposome based transfection method with linearized DNA of pI2G-Hygro plasmids including the coding sequences for FVIII derivatives. Each transfection was performed using 2 µg of DNA per 10 cm diameter dish. At 48 h post-transfection, medium was removed, the cells were trypsinized, diluted and cultured in DMEM selection medium containing hygromycin (500 µg/ml) and 10% fetal calf serum. After two weeks, individual clones, resistant to the selective medium, were isolated and expanded further in selective medium and then frozen for future studies. The secretion of FVIII derivatives was monitored by measuring the ability of FVIII derivatives to function as a cofactor for the Factor IXa-dependent conversion of Factor X into Factor Xa, employing a chromogenic substrate for Factor Xa (Coatest Factor VIII, Chromogenix, Sweden).

Example 5C

Demonstration of Single Chain FVIII Expression in HEK293 Cells

Figure 5:
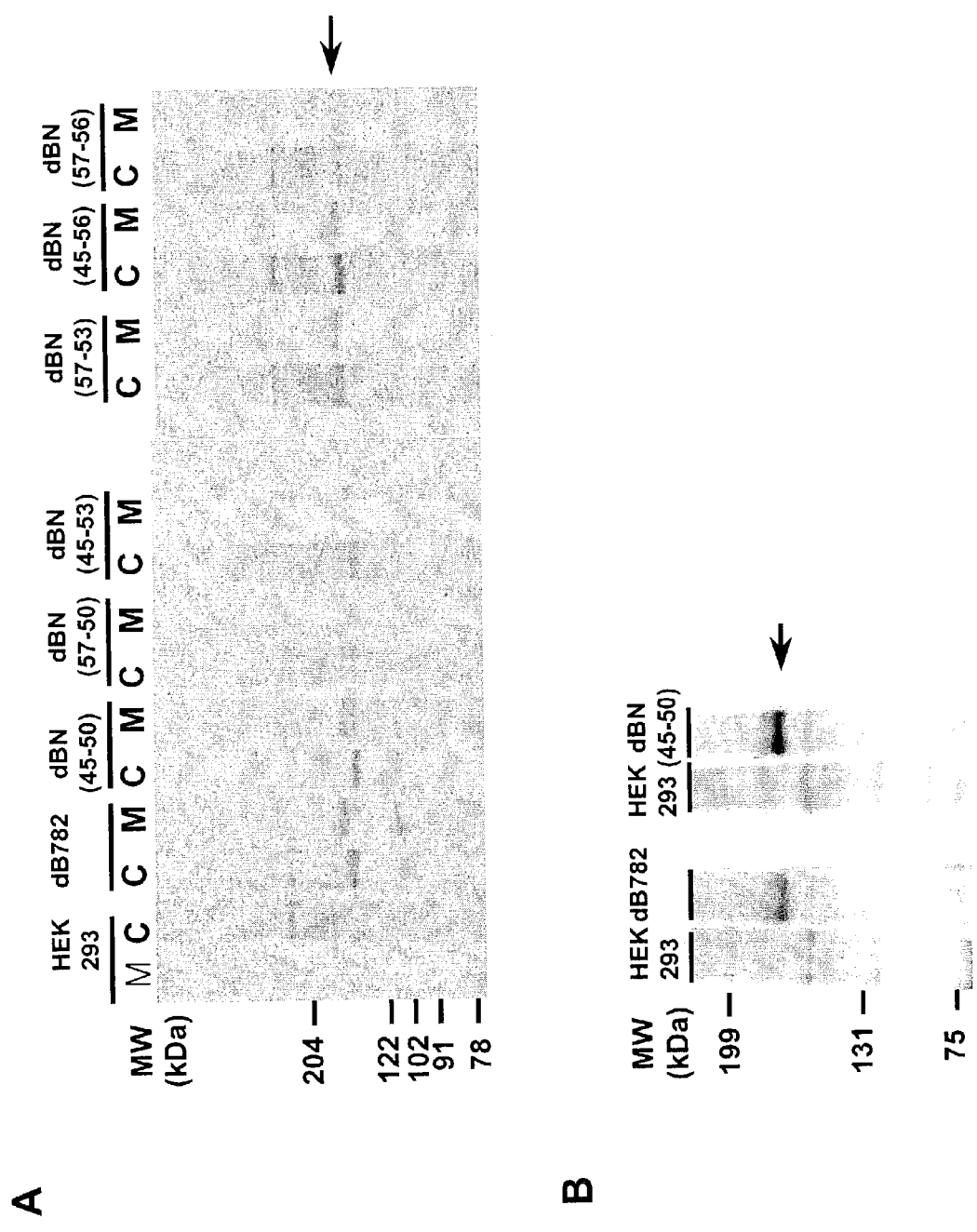
FIGS. 5A–5C show synthesis, secretion, and thrombin cleavage of FVIII derivatives expressed in HEK293 cells.
Figure 5:
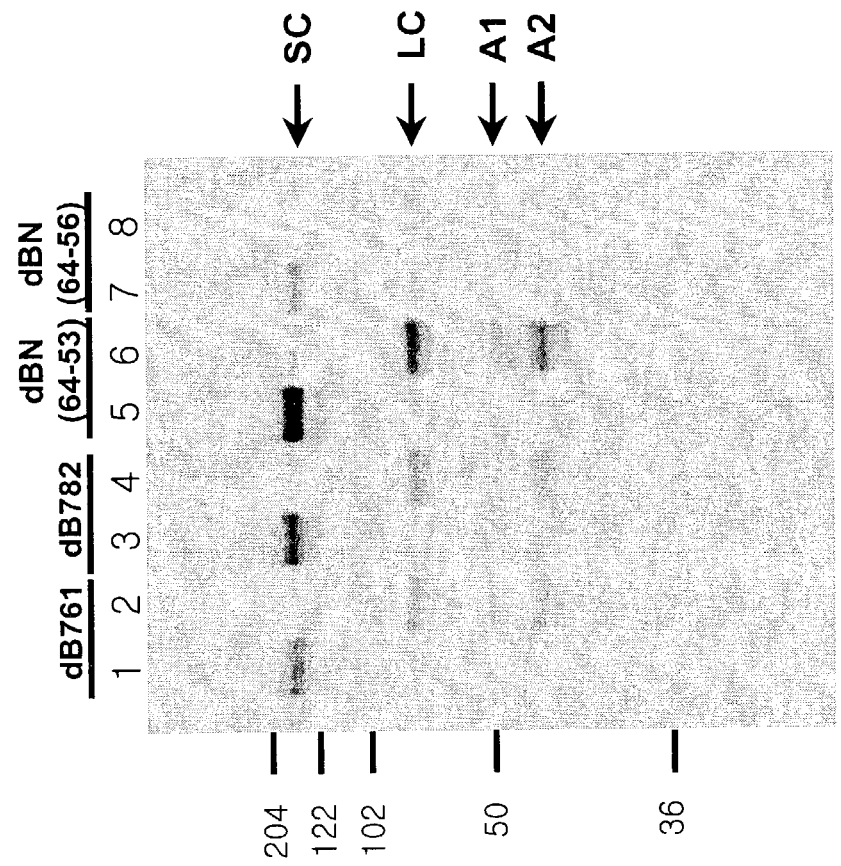

In order to demonstrate that the FVIII derivatives were secreted into culture media as a single chain polypeptide, stably transfected HEK293 cells were grown in the media supplemented with $^{35}$S-methionine for 6 hrs. The conditioned media and cell extracts were then prepared for analysis by immunoprecipitation and SDS-polyacrylamide gel electrophoresis (FIG. 5A). The migration of the FVIII derivatives from the cell extracts (C) and conditioned medium (M) is shown. The names of each FVIII derivatives are indicated on the top. The results demonstrate that the FVIII derivatives which were generated by the fusing of A1, A2, and B domains to the amino acid sequence in the A3 domain beyond Arg-1648, an intracellular processing site, did not affect the synthesis or secretion of the FVIII derivatives from the cell. The predominant FVIII species produced was a single chain molecule of approximately 170 kDa. For immunoblotting for FVIII antigen, media containing the recombinant Factor VIII derivatives dB782 and dBN(45-50) as well as media from normal HEK293 control cells were concentrated approximately 100-fold using Centricon 30,000 MWCO on the day of harvest.

FVIII concentration was measured using an ELISA method. Concentrates were then separated by SDS-PAGE and analyzed by immunoblotting using a monoclonal antibody (ESH-8). As shown in FIG. 5B, ESH-8 antibody used in Western blotting detected a major protein, migrating to approximately 170 kDa, which is similar to results from the metabolic labeling experiment in FIG. 5A.

These results indicate that the FVIII derivatives in this invention are present in culture media mainly in an unprocessed, single-chain form of the FVIII molecule. FIG. 5C depicts thrombin activation of FVIII derivatives. $^{35}$S-methionine labeled FVIII derivatives were immunoprecipitated from the chase conditioned medium of stably expressing HEK293 cells and were divided into equal aliquots and incubated in the absence (lanes 1, 3, 5, and 7) or presence (lanes 2, 4, 6, and 8) of thrombin (1 U/mL) for 30 min at 37° C. Reactions were terminated with SDS-PAGE sample buffer and protein fragments were separated by 10% SDS-PAGE. FVIII protein forms are indicated at the right as follows: SC, single chain; A1, and A2, thrombin-cleaved heavy chain fragments; LC, thrombin-cleaved light chain. The names of each FVIII derivatives are indicated on the top. Analysis of the radiolabeled protein after thrombin digestion indicated a normal appearance of the 73 kD, and 50 and 40 kd fragments corresponding to the molecular sizes of thrombin-cleaved light chain, A1 and A2 domains, respectively. This result demonstrated that single chain FVIII derivatives are cleaved and then activated in the similar pattern as the native or full-length FVIII proteins. These single-chain FVIII derivatives may be advantageous in that they may be produced in more homogeneous forms and may have an improved stability to natural human or other recombinant FVIII proteins.

Example 6

Establishment of CHO Cell Lines Expressing FVIII Derivatives

Example 6A

Construction of Plasmids

Figure 6:
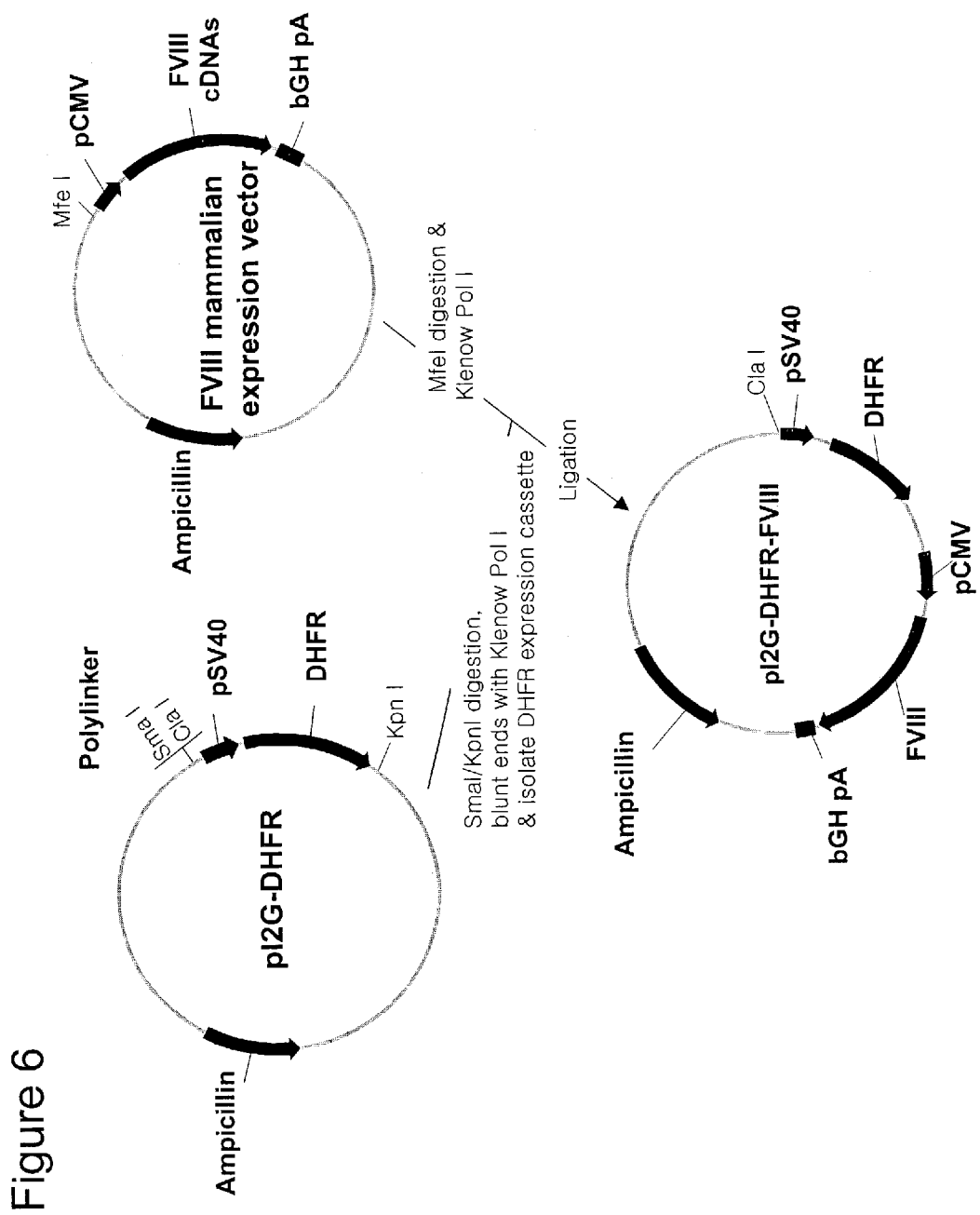
FIG. 6 shows DNA construction scheme for FVIII polypeptide in a mammalian vector.

The plasmids for the establishment of stably transfected CHO cell lines were constructed by the insertion of an expression cassette called pI2G-DHFR comprising the promoter sequences of SV40, the gene coding for the DHFR selection marker, and the SV40 late polyadenylation signal sequences into the single Mfe I site of the maimmnalian expression vectors described in Example 3. The ends liberated by the Mfe I digestion were made blunt by treatment with the Klenow fragment of DNA polymerase I. The subcloning procedure is depicted in FIG. 6.

Example 6B

Transfection of CHO Cells with Plasmids

CHO cells were transfected with the linearized DNA of plasmids pl2G-DHFR including coding sequences for dB782 by a liposome-based transfection method, with 1 or 2 ug of DNA per 10 cm diameter dish. Forty eight hours after the transfection, the cells are trypsinized, diluted and incubated in IMDM selective medium including 10% dialyzed fetal calf serum without hypoxanthinie, thymidine, and xanthine. After two weeks, the clones resistant to the selective medium were subcultured to 1-ml and then 2-ml cups. When the cells reached 70% confluence, the medium was removed and the cell lawns were washed and replenished with fresh medium containing 5% of inactivated serum (to avoid a high background in the coagulation tests). After 24 hours, the medium was harvested and analyzed for the procoagulant activity of FVIII. Biologically active human FVIII was quantified in culture supernatant samples by the standard coagulation or clotting assay (so-called activated partial thromboplastin time) using FVIII-deficient plasma as previously described (Veldkamp et al., Thromb. Diath. Haemorrh. 1968, 19: 279). Results of Factor VIII activity in cells resistant to increasing concentrations of MTX are presented in Table 5.

TABLE 5

Comparison of the FVIII procoagulant activity (FVIII: C) from CHO/DBX11 cells transfected with the mammalian expression vector, pl2G-dhfr-dB782, containing a coding sequence for dB782 before and after gene-amplification with MTX

| MTX (µM) | MU/ml/24 hours of FVIII: C |
| --- | --- |
| 0 | <1.0 |
| 0.02 | 4.94 |
| 0.08 | 16.8 |
| 0.3 | 129 |
| 1.0 | 540 |
| 5.0 | 2900 |

Example 7

Activation of Recombinant Full-length FVIII and FVIII Derivatives by Thrombin

Recombinant full-length FVIII and FVIII derivatives were compared in a study of kinetics of activation by thrombin. The activation was measured in a classical coagulation test (APTT) after incubation in the presence of a catalytic amount of thrombin.

FIGS. 7A and 7B show a comparison of thrombin activation kinetics of the recombinant human FVIII (rH FVIII) and FVIII derivatives. Some FVIII derivatives are activated more strongly with a 7-fold increases after 5 minutes incubation with thrombin. Two FVIII derivatives, dBN(64–53) and dBN(64–56), are activated in the same manner as rh FVIII. While some of FVIII derivatives have higher activation folds, they are not activated more rapidly than the other derivatives or full-length FVIII, thereby showing that FVIII derivatives are not preactivated. This is important for the purpose of its therapeutic use.

The higher activation folds of some derivatives by thrombin can be explained by their lower activation threshold. Smaller amounts of thrombin generated at a site of vascular injury can cause the increased activation of FVIII derivatives, enabling these derivatives to act as procoagulant molecules with an increased efficiency as compared to other derivatives with FVIII activity. In other words, FVIII derivatives except for dBN(64-53) and dBN(64-56) can be activated at a much earlier event in the events of blood coagulation. As a consequence, FVIII derivatives with higher activation folds can be administered to Hemophilia A patients at a much lower dose and at a reduced frequency than other molecules with FVIII activity. This significantly reduces the risk of inhibitory antibody production in the patients. In addition, this also further reduces production and medication costs.

All of the references cited herein are incorporated by reference in their entirety.

Those skilled in the art will recognize, or be able to ascertain using no more than routine experimentation, many equivalents to the specific embodiments of the invention specifically described herein. Such equivalents are intended to be encompassed in the scope of the claims.

What is claimed is:

1. A Factor VIII polypeptide comprising an internal deletion of amino acids from residue 741 to residue 1688, with reference to full-length human factor VIII amino acid sequence of SEQ ID NO:1, wherein the internal deletion is amino acid positions 746 to 1649, 746 to 1652, 746 to 1655, 758 to 1649, 758 to 1652, 758 to 1655, 765 to 1649, 765 to 1652, 765 to 1655, 748 to 1658, 755 to 1658, 762 to 1658, 769 to 1658, 776 to 1658, or 783 to 1658.

2. A pharmaceutical composition comprising the Factor VIII polypeptide of claim 1 and a pharmaceutically acceptable carrier thereof.

3. A lyophilized composition comprising the Factor VIII polypeptide according to claim 1.

4. A method of clotting blood in a subject, comprising contacting a clotting effective amount of the Factor VIII polypeptide of claim 1 with the blood.

5. A method of treating Hemophilia A in a patient, comprising administering a clotting effective amount of the Factor VIII polypeptide of claim 1 to a patient in need thereof.

6. A Factor VIII polypeptide comprising an internal deletion of one or more amino acids from residue 741 to residue 1688, with reference to full-length human factor VIII amino acid sequence of SEQ ID NO: 1, wherein praline at position 739 is replaced by another amino acid.

7. A pharmaceutical composition comprising the Factor VIII polypeptide of claim 6 and a pharmaceutically acceptable carrier thereof.

8. A lyophilized composition comprising the Factor VIII polypeptide according to claim 6.

9. A Factor VIII polypeptide comprising an internal deletion of amino acids from residue 746 to residue 1655, with reference to full-length human factor VIII amino acid sequence of SEQ ID NO:1, wherein the internal deletion is amino acid positions 746 to 1649, 746 to 1652, 746 to 1655, 758 to 1649, 758 to 1652, 758 to 1655, 765 to 1649, 765 to 1652, 765 to 1655, further comprising tripeptide sequence (Asn-X-Thr or Asn-X-Ser where X can be any amino acid) encompassing fusion sites between Asn amino acid at positions 745, 757, or 764, and Thr or Set amino acid at positions 1651, 1654, or 1657.

10. A pharmaceutical composition comprising the Factor VIII polypeptide of claim 9 and a pharmaceutically acceptable carrier thereof.

11. A lyophilized composition comprising the Factor VIII polypeptide according to claim 9.

* * * * *